US011767499B2

(12) United States Patent
Martin et al.

(10) Patent No.: US 11,767,499 B2
(45) Date of Patent: Sep. 26, 2023

(54) CELL CULTURE VESSEL

(71) Applicant: CORNING INCORPORATED, Corning, NY (US)

(72) Inventors: Gregory Roger Martin, Acton, ME (US); Ana Maria Del Pilar Pardo, Portsmouth, NH (US); Michael Kurt Schaefer, Gorham, ME (US); Allison Jean Tanner, Portsmouth, NH (US)

(73) Assignee: CORNING INCORPORATED, Corning, NY (US)

(*) Notice: Subject to any disclaimer, the term of this patent is extended or adjusted under 35 U.S.C. 154(b) by 828 days.

(21) Appl. No.: 16/628,810

(22) PCT Filed: Jul. 13, 2018

(86) PCT No.: PCT/US2018/042161
§ 371 (c)(1),
(2) Date: Jan. 6, 2020

(87) PCT Pub. No.: WO2019/014636
PCT Pub. Date: Jan. 17, 2019

(65) Prior Publication Data
US 2020/0131461 A1 Apr. 30, 2020

Related U.S. Application Data

(60) Provisional application No. 62/532,671, filed on Jul. 14, 2017.

(51) Int. Cl.
*C12M 3/06* (2006.01)
*B01L 3/00* (2006.01)
(Continued)

(52) U.S. Cl.
CPC ....... *C12M 23/16* (2013.01); *B01L 3/502715* (2013.01); *C12M 23/08* (2013.01);
(Continued)

(58) Field of Classification Search
CPC ...... C12M 23/16; C12M 23/08; C12M 23/24; C12M 23/12; C12M 29/04;
(Continued)

(56) References Cited

U.S. PATENT DOCUMENTS 2,947,116 A 8/1960 Earle et al.
3,630,849 A 12/1971 Land et al.
(Continued)

FOREIGN PATENT DOCUMENTS

AU 2004256209 A1 1/2005
CA 2558946 A1 1/2005
(Continued)

OTHER PUBLICATIONS

Achilli et al, "Advances in the Formation, Use and Understanding of Multi-Cellular Spheroids", Expert Opin. Biol. Ther. (2012) 12(10):1347-1360.
(Continued)

*Primary Examiner* — Michael L Hobbs
(74) *Attorney, Agent, or Firm* — Chandra J. Duncan

(57) ABSTRACT

A cell culture vessel (100) includes a wall including an inner surface defining a cell culture chamber of the vessel. A substrate (215) of non-porous material is positioned in the cell culture chamber between a first region of the cell culture chamber and a second region of the cell culture chamber. The substrate includes a plurality of microcavities (220), each microcavity of the plurality of microcavities includes a concave surface defining a well and an opening, the concave surface of each microcavity includes at least one aperture including a dimension less than or equal to about 15 microns defining a path from the well to the second region. A cell culture vessel including a substrate including a plurality of (Continued)

microcavities and a layer of porous material is also provided. Methods of culturing cells in the cell culture vessel are also provided.

34 Claims, 11 Drawing Sheets

(51) Int. Cl.
    *C12M 1/24*         (2006.01)
    *C12M 1/04*         (2006.01)
    *C12M 1/00*         (2006.01)

(52) U.S. Cl.
    CPC ............ *C12M 23/24* (2013.01); *C12M 29/04* (2013.01); *B01L 2300/0681* (2013.01); *B01L 2300/12* (2013.01)

(58) Field of Classification Search
    CPC ....... B01L 3/502715; B01L 2300/0681; B01L 2300/12
    See application file for complete search history.

(56) References Cited

U.S. PATENT DOCUMENTS

| | | |
|---|---|---|
| 4,670,396 A | 6/1987 | Bear et al. |
| 4,927,764 A | 5/1990 | Lyman et al. |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,374,557 A | 12/1994 | Verma |
| 5,487,872 A | 1/1996 | Hafeman et al. |
| 5,554,536 A | 9/1996 | Rising |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,759,494 A | 6/1998 | Szlosek |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,767,607 B2 | 7/2004 | Tanner et al. |
| 6,811,752 B2 | 11/2004 | Barbera-Guillem |
| 6,908,767 B2 | 6/2005 | Bader |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,493,733 B2 | 11/2016 | Giles |
| 9,494,577 B2 | 11/2016 | Mcgarr et al. |
| 9,573,128 B1 | 2/2017 | McClelland |
| 9,587,213 B2 | 3/2017 | Morgan et al. |
| 9,732,317 B2 | 8/2017 | Wilson |
| 9,790,465 B2 | 10/2017 | Bennett et al. |
| 9,845,451 B2 | 12/2017 | Martin et al. |
| 9,862,918 B2 | 1/2018 | Ito |
| 10,254,274 B2 | 4/2019 | Miklas et al. |
| 2002/0022219 A1 | 2/2002 | Clements et al. |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2005/0032208 A1 | 2/2005 | Oh et al. |
| 2005/0047971 A1 | 3/2005 | Clements et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2008/0118974 A1 | 5/2008 | Martin et al. |
| 2008/0206857 A1 | 8/2008 | Kenney et al. |
| 2008/0300278 A1 | 12/2008 | Torrens Jover et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 | 12/2009 | Cattadoris et al. |
| 2009/0298166 A1 | 12/2009 | Fang et al. |
| 2010/0068793 A1 | 3/2010 | Ungrin et al. |
| 2010/0093075 A1 | 4/2010 | Muller |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0129923 A1 | 6/2011 | Wilson et al. |
| 2012/0064627 A1 | 3/2012 | Khine et al. |
| 2012/0129208 A1 | 5/2012 | Khine et al. |
| 2012/0129257 A1 | 5/2012 | Yu et al. |

(56) References Cited

U.S. PATENT DOCUMENTS

| | | |
|---|---|---|
| 2012/0219572 A1 | 8/2012 | Prockop et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |
| 2013/0164848 A1 | 6/2013 | Naka et al. |
| 2013/0203159 A1 | 8/2013 | Itoh et al. |
| 2013/0344598 A1 | 12/2013 | Nistor |
| 2014/0099717 A1 | 4/2014 | Fraker et al. |
| 2014/0106394 A1 | 4/2014 | Ko et al. |
| 2014/0106452 A1 | 4/2014 | Vukasinovic |
| 2014/0120573 A1 | 5/2014 | Tavana et al. |
| 2014/0221225 A1 | 8/2014 | Danen et al. |
| 2014/0227784 A1 | 8/2014 | Ejiri et al. |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Tsukada et al. |
| 2015/0072405 A1 | 3/2015 | Ito |
| 2015/0184119 A1 | 7/2015 | Tsukada et al. |
| 2015/0247112 A1 | 9/2015 | Orr et al. |
| 2016/0003796 A1 | 1/2016 | Kranbuehl |
| 2016/0017267 A1 | 1/2016 | Hansen et al. |
| 2016/0137962 A1 | 5/2016 | Ejiri et al. |
| 2016/0194588 A1 | 7/2016 | Guenat et al. |
| 2016/0216250 A1 | 7/2016 | Ritter et al. |
| 2017/0073625 A1 | 3/2017 | Kasuto et al. |
| 2017/0226455 A1 | 8/2017 | Fang et al. |
| 2017/0283757 A1 | 10/2017 | Carter et al. |
| 2017/0306281 A1 | 10/2017 | Martin et al. |
| 2017/0342363 A1* | 11/2017 | Fang .................. C12M 3/065 |
| 2018/0201888 A1* | 7/2018 | Miwa .................. C12M 23/34 |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1234112 A | 11/1999 |
| CN | 1875093 A | 12/2006 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| DE | 10019862 A1 | 11/2001 |
| DE | 202006017853 U1 | 2/2007 |
| DE | 102009005526 A1 | 7/2010 |
| DE | 102014214077 A1 | 1/2016 |
| DE | 102014017728 A1 | 6/2016 |
| EP | 307048 A2 | 3/1989 |
| EP | 0605527 A1 | 7/1994 |
| EP | 0681846 A2 | 11/1995 |
| EP | 0800571 A2 | 10/1997 |
| EP | 834552 A1 | 4/1998 |
| EP | 965633 A1 | 12/1999 |
| EP | 1181349 A1 | 2/2002 |
| EP | 1348533 A2 | 10/2003 |
| EP | 1445022 A2 | 8/2004 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 * | 10/2016 | ............ C12M 23/12 |
| EP | 3081627 A1 | 10/2016 |
| EP | 3351615 A1 | 7/2018 |
| EP | 3372666 A1 | 9/2018 |
| GB | 2147100 A | 5/1985 |
| JP | 06327462 A | 11/1994 |
| JP | 09173049 A | 7/1997 |
| JP | 10210866 A | 8/1998 |
| JP | 10210966 A | 8/1998 |
| JP | 2003135056 A | 5/2003 |
| JP | 2003180335 A | 7/2003 |
| JP | 2004129558 A | 4/2004 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009050194 A | 3/2009 |
| JP | 2010088347 A | 4/2010 |
| JP | 2010104327 A | 5/2010 |
| JP | 2010-518879 A | 6/2010 |
| JP | 2010158214 A | 7/2010 |
| JP | 2011-509686 A | 3/2011 |
| JP | 2011-521642 A | 7/2011 |
| JP | 2011172533 A | 9/2011 |
| JP | 2012249547 A | 12/2012 |
| JP | 2013055911 A | 3/2013 |
| JP | 2014132869 A | 7/2014 |
| JP | 2015012827 A | 1/2015 |
| JP | 2015073520 A | 4/2015 |
| JP | 5845185 B2 | 1/2016 |
| JP | 2016136921 A | 8/2016 |
| JP | 2017-532970 A | 11/2017 |
| KR | 1020140113139 A | 9/2014 |
| KR | 10-2014-0125662 A | 10/2014 |
| WO | 1992007063 A2 | 4/1992 |
| WO | 93/07258 A1 | 4/1993 |
| WO | 96/21851 A2 | 7/1996 |
| WO | 9815355 A2 | 4/1998 |
| WO | 1998031466 A1 | 7/1998 |
| WO | 2001080997 A1 | 11/2001 |
| WO | 2001092462 A1 | 12/2001 |
| WO | 2004/044120 A2 | 5/2004 |
| WO | 2004/094060 A1 | 11/2004 |
| WO | 2005047464 A2 | 5/2005 |
| WO | 2006043267 A1 | 4/2006 |
| WO | 2007/015770 A1 | 2/2007 |
| WO | 2007097120 A1 | 8/2007 |
| WO | 2008/008149 A2 | 1/2008 |
| WO | 2008/106771 A1 | 9/2008 |
| WO | 2008118500 A1 | 10/2008 |
| WO | 2008153783 A1 | 12/2008 |
| WO | 2009094125 A2 | 7/2009 |
| WO | 2009148509 A1 | 12/2009 |
| WO | 2009148512 A2 | 12/2009 |
| WO | 2010008566 A2 | 1/2010 |
| WO | 2012036011 A1 | 3/2012 |
| WO | 2012170232 A1 | 12/2012 |
| WO | 2013042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014072432 A1 | 5/2014 |
| WO | 2014/140181 A1 | 9/2014 |
| WO | 2014156455 A1 | 10/2014 |
| WO | 2014165273 A1 | 10/2014 |
| WO | 2014171782 A1 | 10/2014 |
| WO | 2014/179196 A1 | 11/2014 |
| WO | 2014196204 A1 | 12/2014 |
| WO | 2015033507 A1 | 3/2015 |
| WO | 2015/061907 A1 | 5/2015 |
| WO | 2016064757 A1 | 4/2016 |
| WO | 2016069885 A1 | 5/2016 |
| WO | 2016069892 A1 | 5/2016 |
| WO | 2016069895 A1 | 5/2016 |
| WO | 2016069917 A1 | 5/2016 |

(56) References Cited

FOREIGN PATENT DOCUMENTS

| | | |
|---|---|---|
| WO | 2016069930 A1 | 5/2016 |
| WO | 2017025584 A1 | 2/2017 |
| WO | 2017/047735 A1 | 3/2017 |
| WO | 2017/077163 A1 | 5/2017 |
| WO | 2017142410 A1 | 8/2017 |
| WO | 2018200893 A1 | 11/2018 |
| WO | 2019014621 A1 | 1/2019 |
| WO | 2019014627 A1 | 1/2019 |
| WO | 2019014635 A1 | 1/2019 |
| WO | 2019014636 A1 | 1/2019 |
| WO | 2019178039 A1 | 9/2019 |

OTHER PUBLICATIONS

Alepee et al, "State-Of-The-Art 3D Cultures (Organs-On-A-Chip) in Safety Testing and Pathophysiology"; Transatlantic Think Tank for Toxicology, T4 Workshop Report, ALTEX 31, Apr. 2014, pp. 441-477, Retrieved From: http://dx.doi.org/10.14573/altex1406111 (Jul. 14, 2014).

Aline, "We Engineer Microfluidic Products"; 7 Pages; (2020) https://alineinc.com/.

G-Plate: Accelerate your cell cultures to the next dimension, "An original cell culture model allowing for island-shaped 3D cell aggregates", 1 page, retrieved Sep. 8, 2015.

Anada et al, "An Oxygen-Permeable Spheroid Culture System for the Prevention of Central Hypoxia and Necrosis of Spheroids"; Biomaterials 33 (2012) 8430-8441.

Bartosh et al, "Aggregation of Human Mesenchymal Stromal Cells (MSCS) Into 3D Spheroids Enhances Their Antiinflammatory Properties"; PNAS, Aug. 3, 2010, 107 (31):13724-13729.

Bioivt Elevating Science ®; 6 Pages; (2020); http://www.hepregen.com/.

Carver et al, "Multicellular Tumor Spheroids as a Model for Assessing Delivery of Oligonucleotides in Three Dimensions"; Molecular Therapy-Nucleic Acids (2014) 3, E153; 8 Pages.

Chen et al, "Microfluidic array for three-dimensional perfusion culture of human mammary epithelial cells" Biomedical Microdevices, 2011, 13(4):753-758.

Cheng et al, "MicroRNA-34a Targets Forkhead Box J2 To Modulate Differentiation of Endothelial Progenitor Cells in Response To Shear Stress", J Mol Cell Cardiol. 74 (2014) 4-12.

Choi et al, "Feasibility of a simple double-layered coculture system incorporating metabolic processes of the intestine and liver tissue: application to the analysis of benzo[a]pyrene toxicity", Toxicology in Vitro 18 (2004) 393-402.

CN-Bio, "Transforming Drug Discovery and the Lives of Patients"; 5 Pages; (2020) http://cn-bio.com/.

Colazzo et al., "Shear Stress and Vegf Enhance Endothelial Differentiation of Human Adipose-Derived Stem Cells", Growth Factors, 2014, 32(5):139-149.

Corning® HTS Transwell®-96 Tissue Culture Systems, Permeable Supports for High Throughput Screening Applications; 2 Pages (2004).

Tissue Dynamics, "Disruptive Drug Development"; 3 Pages; (Downloaded Mar. 9, 2020); https://www.tissuedynamics.com/.

Dolznig et al., "Organotypic spheroid cultures to study tumor-stroma interaction during cancer development", Drug Discovery Today: Disease Models, 2011, 8(2-3):113-118.

Domansky et al., "Perfused Multiwell Plate for 3D Liver Tissue Engineering", Lab Chip, 2010, 10:51-58.

Emulate, 6 Pages; (2019) https://emulatebio.com/.

Tissuse, "Emulating Human Biology, Pioneering Human-On-A-Chip Developments"; 1 Page; (Downloaded Mar. 9, 2020) https://www.tissuse.com/en/.

Endo et al, "Gene transfection to spheroid culture system on micropatterned culture plate by polyplex nanomicelle: a novel platform of genetically-modified cell transplantation", Drug Deliv. and Transl. Res., 2012, 2:398-405.

Engelberg et al, "Essential operating principles for tumor spheroid growth", BMC Systems Biology 2008, 2:110, 19 pages.

Friedrich et al, "Experimental anti-tumor therapy in 3-D: spheroids—old hat or new challenge?" Int J Radiat Biol 2007, 83(11-12):849-871.

Friedrich et al, "Spheroid-based drug screen: considerations and practical approach", Nature protocols, 2009, 4(3):309-323.

Frith et al, "Dynamic three-dimensional culture methods enhance mesenchymal stem cell properties and increase therapeutic potential", Tissue engineering, 2010, 16(4):735-749.

Fukuda et al, "Efficacy of a polyurethane foam/spheroid artificial liver by using human hepatoblastoma cell line (Hep G2)", Cell Transplantation, 2003, 12:51-58.

GeoCHEM Incorporated, Product Line; https://www.geocheminc.com, 4 Pages; (2020).

Haycock, "3D cell culture: a review of current approaches and techniques", Methods Mol Biol, 2011; 695:1-15.

Hirschhaeuser et al, "Multicellular tumor spheroids: An underestimated tool is catching up again", Journal of Biotechnology 148 (2010) 3-15.

Howes et al, "3-Dimensional Culture Systems for Anti-Cancer Compound Profiling and High-Throughput Screening Reveal Increases in EGFR Inhibitor-Mediated Cytotoxicity Compared To Monolayer Culture Systems"; PLOS ONE; Sep. 2004, 9(9), 11 Pages.

Hribar et al., "Nonlinear 3D Projection Printing of Concave Hydrogel Microstructures for Long-Term Multicellular Spheroid and Embryoid Body Culture"; Lab Chip, 2015, 15, 2412-2418.

Hwang et al., "Microwell-Mediated Control of Embryoid Body Size Regulates Embryonic Stem Cell Fate Via Differential Expression of WNT5A and WNT11"; PNAS, 2009, 106(40):16978-16983.

HµREL ® Corporation, Bioanalytic Tools Company; 2 Pages; (2013); http://hurelcorp.com/.

Jeon et al, "Combined Effects of Flow-Induced Shear Stress and Micropatterned Surface Morphology On Neuronal Differentiation of Human Mesenchymal Stem Cells" J Biosci Bioeng, 2014, 117(2):242-247.

Jiang et al, "Shear Enhances Thrombopoiesis and Formation of Microparticles That Induce Megakaryocytic Differentiation of Stem Cells", Blood, Sep. 25, 2014; 124(13):2094-2103.

Kelm et al, "Method for generation of homogeneous multicellular tumor spheroids applicable to a wide variety of cell types", Biotechnology and Bioengineering 2003; 83(2):173-180.

Kim et al, "Shear Stress Induced By an Interstitial Level of Slow Flow Increases the Osteogenic Differentiation of Mesenchymal Stem Cells Through Taz Activation" PLoS ONE, Mar. 21, 2014; 9(3), e92427, 9 pages.

Koide et al., "Formation of multicellular spheroids composed of adult rat hepatocytes in dishes with positively charged surfaces and under other nonadherent environments", Exp Cell Res 1990; 186:227-235.

Kunz-Schughart et al, "The use of 3-D cultures for high-throughput screening: the multicellular spheroid model", J Biomol Screen 2004, 9(4):273-285.

Kutsuzawa et al, "Highly Robust Protein Production By Co-Culture of Cho Spheroids Layered On Feeder Cells in Serum-Free Medium"; Colloid Polym Sci (2014) 292; 839-848.

Labusca, "Scaffold free 3D culture of mesenchymal stem cells; implications for regenerative medicine", J Transplant Stem Cel Biol 2015 2(1): 8.

Landry et al, "Spheroidal aggregate culture of rat liver cells: histotypic reorganization, biomatrix deposition, and maintenance of functional activities" J Cell Biol 1985; 101:914-923.

Lau et al, "Evaluation of a Novel in Vitro CACO-2 Hepatocyte Hybrid System for Predicting In Vivo Oral Bioavailability" Drug Metabolism and Disposition, vol. 32, No. 9, pp. 937-942, 2004.

Liquid Surge Control, LLC; "The Latest in Drop-In Baffle Technology"; 2 Pages; (2019).

Liu et al, "Quasi-spherical microwells on superhydrophobic substrates for long term culture of multicellular spheroids and high throughput assays" Biomaterials 35 (2014) pp. 6060-6068.

Liu et al, "Advanced Micromachining of Concave Microwells for Long Term On-Chip Culture of Multicellular Tumor Spheroids", ACS Appl. Mater. Interfaces, 2014, 6, 8090-8097.

(56) References Cited

OTHER PUBLICATIONS

Lu et al, "Galactosylated PVDF membrane promotes hepatocyte attachment and functional maintenance" Biomaterials 24 (2003) 4893-4903.
Markovitz-Bishitz, "A polymer microstructure array for the formation, culturing, and high throughput drug screening of breast cancer spheroids" Biomaterials 31 (2010) 8436-8444.
Messner et al, Multi-cell type human liver microtissues for hepatotoxicity testing. Archives of Toxicology, Nov. 11, 2012, 5 pages.
Elveflow; "Microfluidics Innovation Center"; 6 Pages; (Downloaded Mar. 9, 2020); https://www.elveflow.com/.
Mironov et al, "Organ Printing: Tissue Spheroids as Buliding Blocks" Biomaterials, 2009; 30 (12): 2164-2174.
Lovett et al. "Vascularization Strategies for Tissue Engineering" Tissue Engineering Part B, 2009, vol. 15, No. 3, pp. 353-370.
Moon et al., "Optimizing Human Embryonic Stem Cells Differentiation Efficiency By Screening Size-Tunable Homogenous Embryoid Bodies"; Biomaterials; 35 (2014) 5987-5997.
Urich et al., "Multicellular Self-Assembled Spheroidal Model of the Blood Brain Barrier" Scientific Reports, 3, 1500, 8 Pages.
Murphy et al, "3D Bioprinting of Tissues and Organs"; Nature Biotechnology, vol. 32, No. 8, Aug. 2014, pp. 773-785.
Mortis; "Bridging the Gap Between In Vitro and In Vivo Research"; 16 Pages; (2015); https://www.nortisbio.com/.
Mimetas the Organ-On-A-Chip Company; "Organ-On-A-Chip Models for Science and Pharma"; 4 Pages; (Downloaded Mar. 9, 2020); https://mimetas.com/.
Otsuka et al, "Two-dimensional multiarray formation of hepatocyte spheroids on a microfabricated PEG-brush surface." ChemBioChem 2004; 5:850-855.
Peshwa et al, "Mechanistics of formation and ultrastructural evaluation of hepatocyte spheroids." In Vitro Cell Dev Biol Anim 1996; 32:197-203.
Organovo, "Pioneering Bioprinted Tissues To Treat Disease"; 2 Pages; (Downloaded Mar. 9, 2020) http://organovo.com/.
Rezende et al., "Scalable Biofabrication of Tissue Spheroids for Organ Printing"; Sciverse Science Direct, Procedia CIRP 5, (2013) 276-281.
Sa et al, "Round-bottomed Honeycomb Microwells: Embryoid body shape correlates with stem cell fate" Journal of Developmental Biology and Tissue Engineering vol. 4(2), pp. 12-22, May 2012.
Sakai et al, "Large-scale preparation and function of porcine hepatocyte spheroids." Int J Artif Organs 1996; vol. 19, No. 5, pp. 294-301.
Sakai et al, "Detachably Assembled Microfluidic Device for Perfusion Culture and Post-Culture Analysis of Spheroid Array"; Biotechnol. J. 2014, 9, 971-979.
Sakai et al, "Technique for the Control of Spheroid Diameter Using Microfabricated Chips"; Sciencedirect, Acta Biomaterialia 3 (2007) 1033-1040.
Sart et al, "Three-dimensional aggregates of mesenchymal stem cells: cellular mechanisms, biological properties and applications" Tissue engineering, 2013, Part B, vol. 00, No. 00, 1-16.
Satoh et al, "A Pneumatic Pressure-Driven Multi-Throughput Microfluidic Circulation Culture System" Lab Chip, 2016, 16, 2339-2348.
Seldon et al, "Evaluation of Encapsulated Liver Cell Spheroids in a Fluidised-Bed Bioartificial Liver for Treatment of Ischaemic Acute Liver Failure in Pigs in a Translational Setting"; Plos One, 2013, 8(12), e82312.
Takezawa et al, "Morphological and immuno-cytochemical characterization of a hetero-spheroid composed of fibroblasts and hepatocytes" J Cell Sci 1992; 101:495-501.
Tara; "Innovating Predictive Cardiac Physiology"; 4 Pages; (2019) http://tarabiosystems.com/.
The Lab Depot® Products for Discovery Lab Supplies; Shake Flasks, 3 and 4 Baffles Product Information; 5 Pages (2019).
Tobe et al, "Receptor-mediated formation of multilayer aggregates of primary cultured adult rat hepatocytes on actose-substituted polystyrene" Biochem Biophys Res Commun 1992; 184(1):225-230.
Tong et al, "Long-term culture of adult rat hepatocyte spheroids." Exp Cell Res 1992; 200:326-332.
Truckenmuller et al, Thermoforming of Film-Based Biomedical Microdevices, Adv. Mater. 2011, 23, pp. 1311-1329.
Tung et al, "High-throughput 3D spheroid culture and drug testing using 384 hanging drop array" Analyst, 2011, 136 (3), 473-478.
Uchida et al, "An Injectable Spheroid System With Genetic Modification for Cell Transplantation Therapy"; Biomaterials, 35 (2014) 2499-2506.
Vinci et al, Advances in establishment and analysis of three-dimensional tumor spheroid-based functional assays tor target validation and drug evaluation, BMC Biology 2012, 10:29.
Weegman et al, "Nutrient Regulation By Continuous Feeding Removes Limitations On Cell Yield in the Large-Scale Expansion of Mammalian Cell Spheroids"; PLOS One, 2013, vol. 8, Issue 10, e76611, 10 Pages.
Wikipedia, "Antiroll Tanks"; 3 Pages; Page Last Edited May 23, 2019.
Wrighton et al, "Forces of Change: Mechanics Underlying Formation of Functional 3D Organ Buds" Cell Stem Cell, May 7, 2015; 16(5): 453-454.
Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-111.
Yamada et al, "Efficient induction of hepatocyte spheroids in a suspension culture using a water-soluble synthetic polymer as an artificial matrix." J Biochem 1998; 123:1017-1023.
AxoSIM, Nerve-On-A-Chip Mini-Brain About Team; 6 Pages; (Downloaded Mar. 9, 2020); http://axosim.com/.
Corning Life Sciences Product Portfolio; 5 Pages Saved Mar. 6, 2020.
Madoux et al., "Building Phenotypic 3D Spheroid Hts Assays To Identify Synthetic Lethal Small Molecule Inhibitors of Kras"; The Scripps Research Institute Molecular Screening Center and Department of Cancer Biology, Scripps Florida, Jupiter, Florida, Department of Pathology, Jupiter Medical Center, Jupiter, Florida.
Stemcell Technologies, Reproducible and Uniform Embryoid Bodies Using AggreWell Plates, StemCell Technologies, Technical Manual Version 3.0.0, Mar. 2011, Catalog #29146, pp. 1-28.

* cited by examiner

US 11,767,499 B2

CELL CULTURE VESSEL

CROSS REFERENCE TO RELATED APPLICATION

This is a national stage application under 35 U.S.C. § 371 of International Application No. PCT/US2018/042161 filed on Jul. 13, 2018, which claims the benefit of priority of U.S. Provisional Application Serial No. 62/532,671 filed on Jul. 14, 2017, entitled "Cell Culture Containers and Methods of Culturing Cells", the contents of which are relied upon and incorporated herein by reference in their entirety.

FIELD

The present disclosure relates generally to a cell culture vessel and methods of culturing cells, and more particularly, to a cell culture vessel having a porous support for culturing three-dimensional cells, and methods of culturing three-dimensional cells in the cell culture vessel.

BACKGROUND

It is known to contain three-dimensional cells in a cell culture vessel. It is also known to culture three-dimensional cells in a cell culture vessel.

SUMMARY

The following presents a simplified summary of the disclosure in order to provide a basic understanding of some exemplary embodiments described in the detailed description.

In embodiments, the disclosure provides a cell culture vessel having a necked opening, a cell culture chamber, a top, a bottom, sidewalls an endwall opposite the necked opening and a surface for culturing cells that has a microcavity array. In embodiments, the surface for culturing cells having a microcavity array is formed, partially or entirely from porous material. In embodiments, the substrate for culturing cells has an array of microcavities on one surface and a porous material on a second surface, and a portion of the walls of the microcavities are provided by porous material. In embodiments, the microcavities have openings to allow gas to pass through the wall of the microcavities.

In additional embodiments, the cell culture vessel has structures for introducing and removing media below the porous material or through the porous material without disturbing the media residing above cells resting in the microcavities of the microcavity array. In additional embodiments, the disclosure provides methods for culturing cells in the cell culture vessel, and methods of introducing and removing cells and media from the vessel.

The above embodiments are exemplary and can be provided alone or in any combination with any one or more embodiments provided herein without departing from the scope of the disclosure. Moreover, it is to be understood that both the foregoing general description and the following detailed description present embodiments of the present disclosure, and are intended to provide an overview or framework for understanding the nature and character of the embodiments as they are described and claimed. The accompanying drawings are included to provide a further understanding of the embodiments, and are incorporated into and constitute a part of this specification. The drawings illustrate various embodiments of the disclosure, and together with the description, serve to explain the principles and operations thereof.

BRIEF DESCRIPTION OF THE DRAWINGS

These and other features, embodiments, and advantages of the present disclosure can be further understood when read with reference to the accompanying drawings in which.

DETAILED DESCRIPTION

Figure 1:
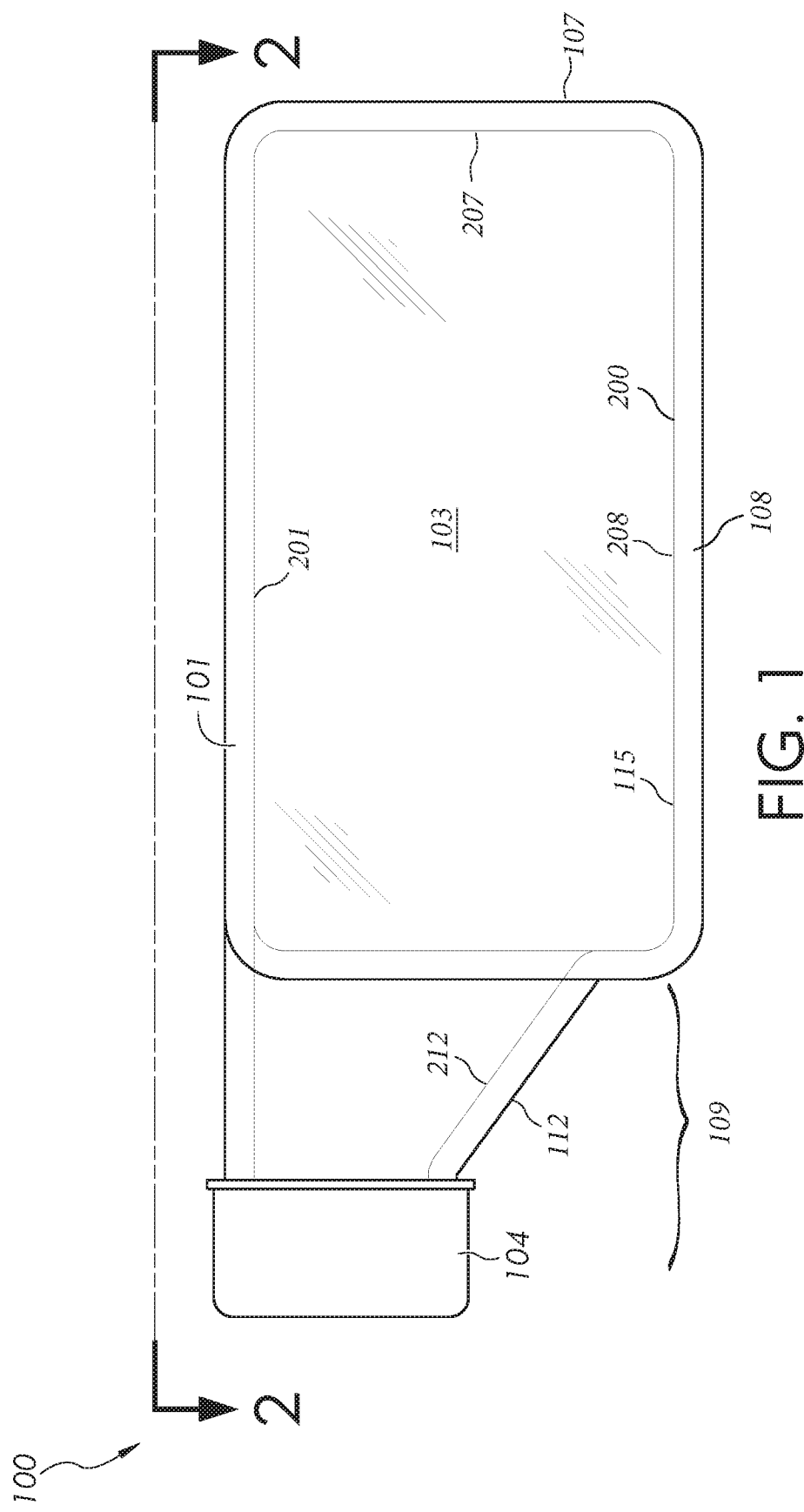
FIG. 1 schematically illustrates a side view of a first exemplary cell culture vessel in accordance with embodiments of the disclosure.

Features will now be described more fully hereinafter with reference to the accompanying drawings in which exemplary embodiments of the disclosure are shown. Whenever possible, the same reference numerals are used throughout the drawings to refer to the same or like parts. However, this disclosure can be embodied in many different forms and should not be construed as limited to the embodiments set forth herein.

A cell culture vessel (e.g., flask) can provide a sterile chamber for culturing cells. In some embodiments, culturing cells can provide information related to the study of diseases and toxicology, the efficacy of medications and treatments, characteristics of tumors, organisms, genetics, and other scientific, biological, and chemical principles of and relating to cells. As compared to two-dimensional cell cultures, in some embodiments, three-dimensional cell cultures can produce multicellular structures that are more physiologically accurate and that more realistically represent an environment in which cells can exist and grow in real life applications as compared to two-dimensional cell culture. For example, three-dimensional cell cultures have been found to more closely provide a realistic environment simulating "in vivo" (i.e. within the living, in a real-life setting) cell growth; whereas two-dimensional cell-cultures have been found to provide an environment simulating "in vitro" (i.e., within the glass, in a laboratory setting) cell growth that is less representative of a real-life environment occurring outside of a laboratory. By interacting with and observing the properties and behavior of three-dimensional cell cultures, advancements in the understanding of cells relating to, for example, the study of diseases and toxicology, the efficacy of medications and treatments, characteristics of tumors, organisms, genetics, and other scientific, biological, and chemical principles of and relating to cells can be achieved.

In embodiments, the cell culture vessel 100 can include a bottom 108, a top 101, and endwall 107 and sidewalls 106, each having internal surfaces that contact liquid media and cells in culture. These internal surfaces define the cell culture chamber 103. At least one of these surfaces can be more particularly adapted for cell growth. For example, a cell culture surface may be treated with a coating to encourage or discourage cells to stick to a surface. Or, to support the culture of spheroid cells, the cell growth surface can include a plurality of microcavities or compartments (e.g., micron-sized wells, submillimeter-sized wells) arranged, for example, in an array. The cell growth surface can be integral to the flask or can be a separate surface having a microcavity array placed or affixed in the cell growth chamber. The top surface, the bottom surface, one or more side surfaces or a combination of these can include microcavities in an array.

For example, in some embodiments, a single spheroid can form in each microcavity of the plurality of microcavities. Cells introduced into the vessel in liquid media will settle into a microcavity by gravity. One or more cells suspended in liquid media will fall through the liquid and settle within each microcavity. The shape of the microcavity (e.g., a concave surface defining a well), and a surface coating of the microcavity that prevents the cells from attaching to the surface can also facilitate growth of cells into three-dimensional form, forming a spheroid in each microcavity.

Microcavities can be, for example, formed in an undulating or sinusoidal shape forming microcavities or microwells having rounded tops and rounded bottoms. These rounded edges may prevent the formation of bubbles when liquid media fills the vessel. In some embodiments, the flask can be filled with a material (e.g., media, solid, liquid, gas) that facilitates growth of three-dimensional cell cultures (e.g., cell aggregates, organoids or spheroids). For example, a media including cells suspended in a liquid can be added to the cell culture chamber or vessel. The suspended cells can collect in the plurality of microcavities by gravity and can form (e.g., grow) into grouping or cluster of cells. The grouped or clustered cells grow in three dimensions to form cells in 3D, otherwise known as a spheroid or an organoid. A single cluster of cells or spheroid forms in a single microcavity. Thus, a vessel, or a cell culture chamber, having a cell culture surface having an array of microcavities, can be used to culture an array of spheroids, each residing in its own microcavity.

During culturing, the spheroids can consume media (e.g., food, nutrients) and produce metabolites (e.g., waste) as a byproduct. Thus, in some embodiments food in the form of media can be added to the cell culture chamber during culturing and waste media can be removed from the cell culture chamber during culturing. This ability to change the media to feed cells and remove waste products, is important for the long-term culture of cells. However, adding and removing media may create turbulence which may disrupt or displace spheroids resting in microcavities. This is especially true when the microcavities are coated with a low binding coating to prevent the cells from sticking to the microcavity surface. The spheroids are loose (not attached to the surface) and may be dislodged and float free of their microcavity resting place. It is not preferable to dislodge spheroids growing in culture for many reasons. The spheroids may be removed from the culture with the removal of spent media. Dislodged spheroids may settle into occupied microcavities, and may merge with other spheroids to form non-uniform 3D cellular structures. That is, after a media change, some spheroids may be bigger than others in the culture. This reduces the uniformity of the cell culture and may affect results of assays or other tests carried out on 3D cells. In this disclosure, structures are disclosed which reduce turbulence, reducing the risk of displacing spheroids from the microcavities, thus promoting the long-term culture of spheroids.

Embodiments of a cell culture vessel 100 and 200 and methods of culturing cells in the cell culture vessel 100 and 200 are described with reference to FIGS. 1-15.

FIG. 1 schematically illustrates a side view of the exemplary cell culture vessel 100. As shown in FIG. 1, an embodiment of a cell culture vessel 100 is shown. The cell culture vessel 100 has a port or aperture 105 (shown in FIG. 1 covered by a cap 104) and a neck 112 connecting the port or aperture 105 to the cell culture chamber 103. In embodiments the aperture can be releasably sealed. For example, in embodiments, the aperture 105 section of the neck 112 can have threads (either interior or exterior) that allow a cap 104 to be releasably sealed 105 by a cap 104 having complimentary threaded structure. Or, the necked opening 105 can be releasably sealed by any other mechanism known in the art to close a vessel. The aperture 105 combined with the neck 112 is the necked opening 109 (See FIG. 3). The necked opening 109 extends through a wall of the cell culture chamber 103 and is in fluid communication with the cell culture chamber 103. The necked opening 113 allows liquid to be introduced and removed from the cell culture chamber (the interior) of the vessel.

The cell culture surface 200 of the vessel 100 is, in embodiments, the interior surface 208 bottom 108 of the vessel 100 when the vessel 100 is oriented for cell growth. In embodiments, the vessel 100 is oriented for cell growth when the vessel 100 is placed with the bottom 108 of the vessel 100 flat on a surface. The vessel 100 may also have sidewalls 106 and an endwall 107 opposite the necked opening 109, a top 101 and bottom 108. In embodiments the top 101 is opposite the cell culture surface 200 of the vessel 100. In embodiments, the necked opening 109 is opposite the endwall 107 of the vessel 100. In embodiments, the cell culture surface 200 has a microcavity array 115. Each of these structures (the necked opening 109, the top 101, the bottom 108, the sidewalls 106 and the endwall 107) of the vessel 100 have internal surfaces facing inside the vessel 100. That is, the top 101 has an interior surface 201. The end wall 107 has an interior surface 207. The sidewalls 106 have interior surfaces 206. The neck 112 has an internal surface 212. The inside of the vessel is the cell culture chamber 103, the space inside the vessel 100, defined by the top 101, the bottom 108, the sidewalls 106 and the endwall 107 where cells reside inside the vessel 100. For example, in some embodiments, the cell culture chamber 103 can include an internal spatial volume of the vessel 103.

Figure 2:
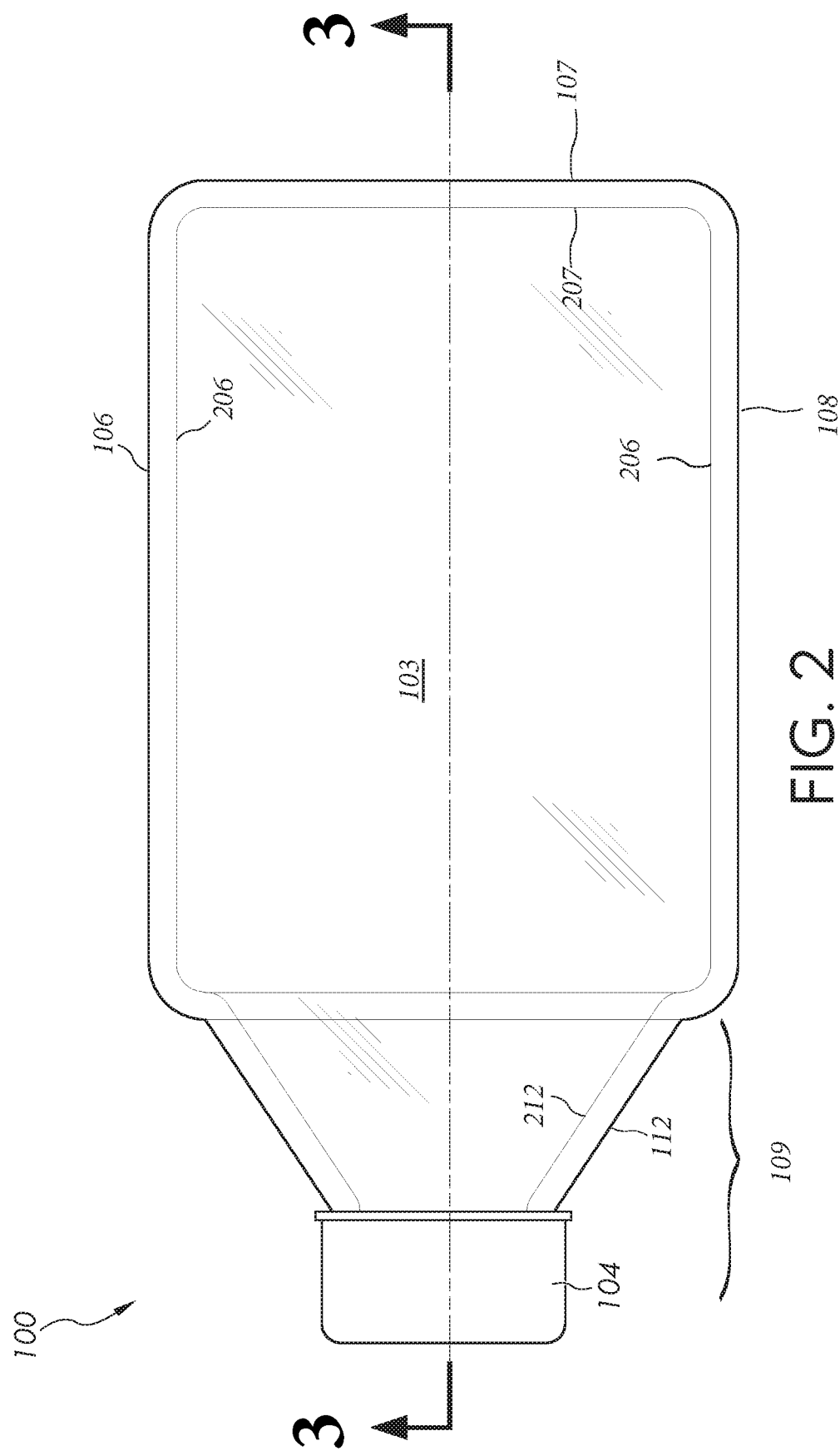
FIG. 2 shows a plan view of the first exemplary cell culture vessel along line 2-2 of FIG. 1 in accordance with embodiments of the disclosure.

FIG. 2 shows a plan view of the vessel 100 along line 2-2 of FIG. 1. In some embodiments, the cell culture vessel 100 can be manufactured from a material including, but not limited to, polymer, polycarbonate, glass, and plastic. In an embodiment, the vessel 100 is illustrated as being manufactured from a clear (e.g., transparent) material; although, in some embodiments, the vessel 100 may, alternatively, be manufactured from a semi-transparent, semi-opaque, or opaque material without departing from the scope of the disclosure.

Turning back to FIG. 1 and FIG. 2, in some embodiments, the vessel 100 can include a cap 104 oriented to cover the aperture 105 to at least one of seal and block the aperture 105, thereby obstructing a path into the cell culture chamber 103 from outside the vessel 100 through the aperture 105. For clarity purposes, the cap 104 is removed and, therefore, not shown in other drawing figures, although it is to be understood that the cap 104 can be provided and selectively added to or removed from the aperture 105 of the vessel 100, in some embodiments, without departing from the scope of the disclosure. In some embodiments, the cap 104 can include a filter that permits the transfer of gas in to and/or out of the cell culture chamber 103 of the vessel 100. For example, in some embodiments, the cap 104 can include a gas-permeable filter oriented to regulate a pressure of gas within the cell culture chamber 103, thereby preventing pressurization (e.g., over-pressurization) of the cell culture chamber 103 relative to a pressure of the environment (e.g., atmosphere) outside the vessel 100.

Figure 3:
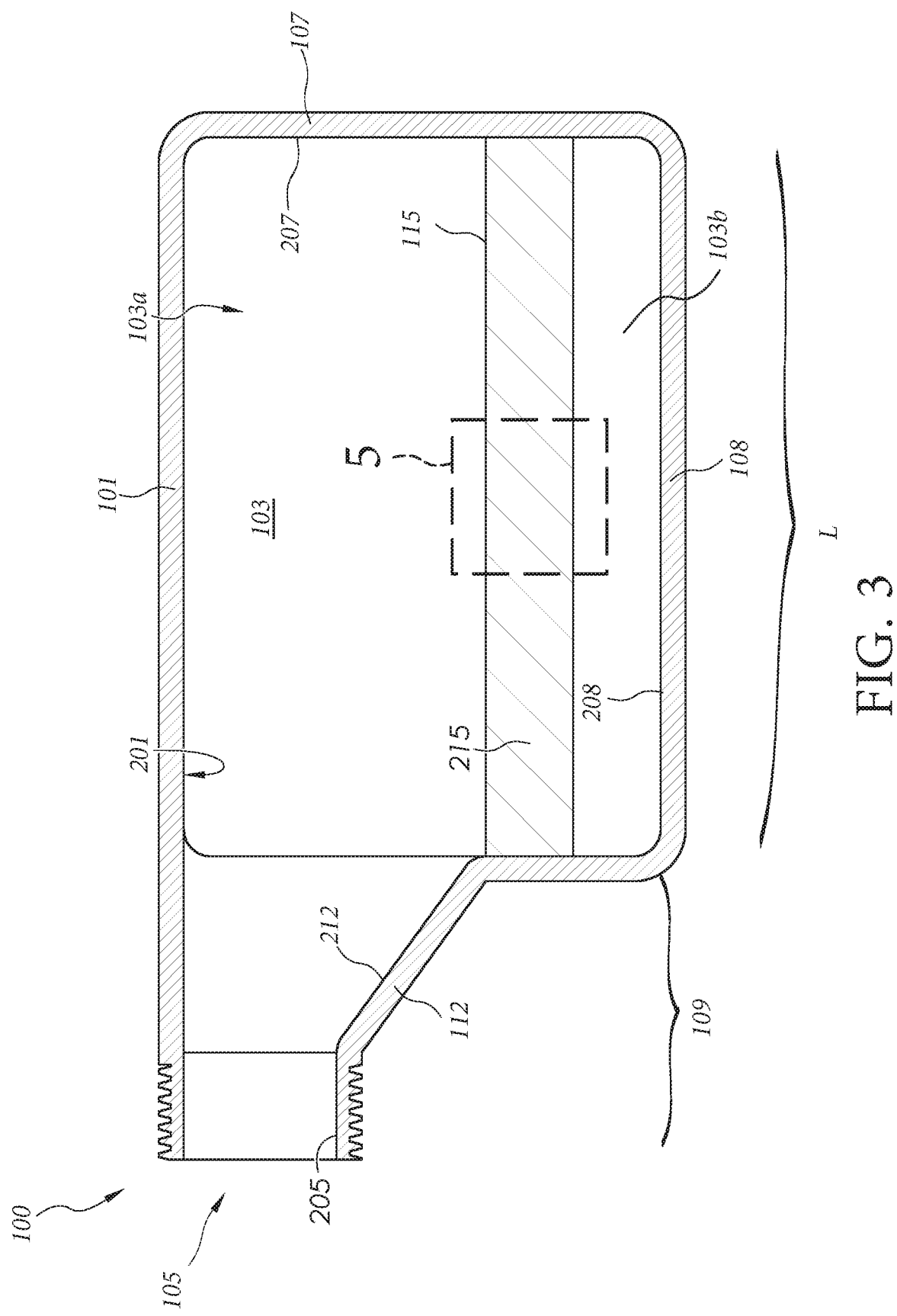
FIG. 3 shows an exemplary cross-sectional view of a cell culture vessel including a cell culture chamber having a first region and a second region in accordance with embodiments of the disclosure.

As shown in FIG. 3, which shows a cross-sectional view along line 3-3 of FIG. 2, in some embodiments, a substrate 215 spans a length "L" of the cell culture chamber 103. Thus, referring to FIG. 3, in some embodiments, the cell culture vessel 100 can include a top 101, a sidewall (not shown in this view), and endwall 107, a bottom 108, a port or aperture 105, a neck 112 and a necked opening 109. Each of these has an internal surface. That is, the top 101 has an internal surface 201, the sidewall (not shown) has an internal surface (also not shown), the endwall 107 has an internal surface 207, the bottom 108 has an internal surface 207, the port or aperture 105 has an internal surface 205, and the neck 112 has an internal surface 212. Also shown is the cell culture chamber 103. Additionally, in embodiments, the vessel 100 can include a substrate 215 of porous material positioned in the cell culture chamber 103 between a first region 103a of the cell culture chamber 103 and a second region 103b of the cell culture chamber 103. That is, the substrate 215 separates the cell culture chamber 103 into an area above the porous material 103a, and an area below the porous material 103b. The vessel 100 can include a first aperture 105 in fluid communication with the first region 103a. In some embodiments, the substrate 215 can include a plurality of microcavities 220 (See FIG. 4-9). In some embodiments, the substrate 215 can be positioned entirely within the cell culture chamber 103 of the vessel 100 and can, therefore, be entirely isolated within a sterile environment of the cell culture chamber 103 with access into and out of the cell culture chamber 103 limited, for example, by the first aperture 105.

Figure 4:
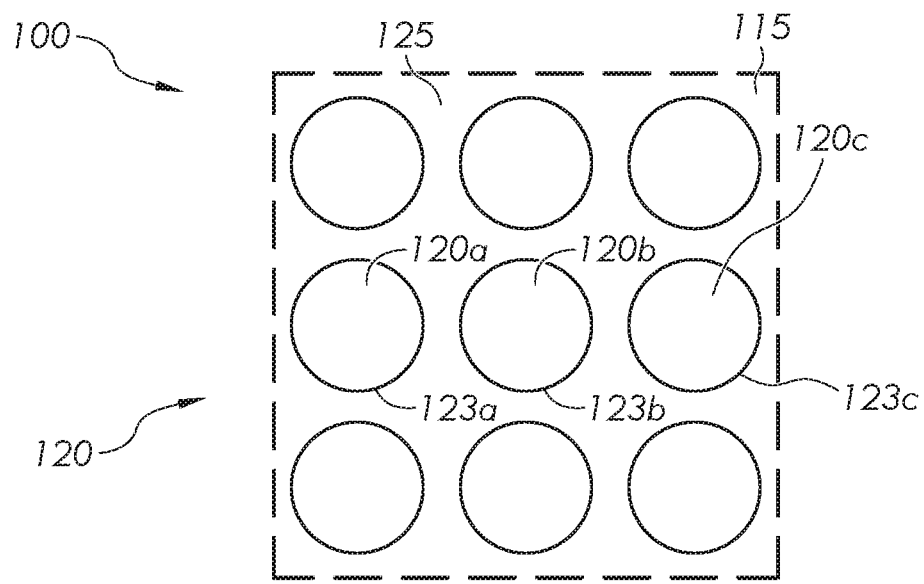
FIG. 4 illustrates an enlarged schematic representation of an exemplary embodiment of the microcavity array of cell culture vessel of FIG. 3 including a substrate including a plurality of microcavities including at least one aperture in accordance with embodiments of the disclosure.
Figure 5:
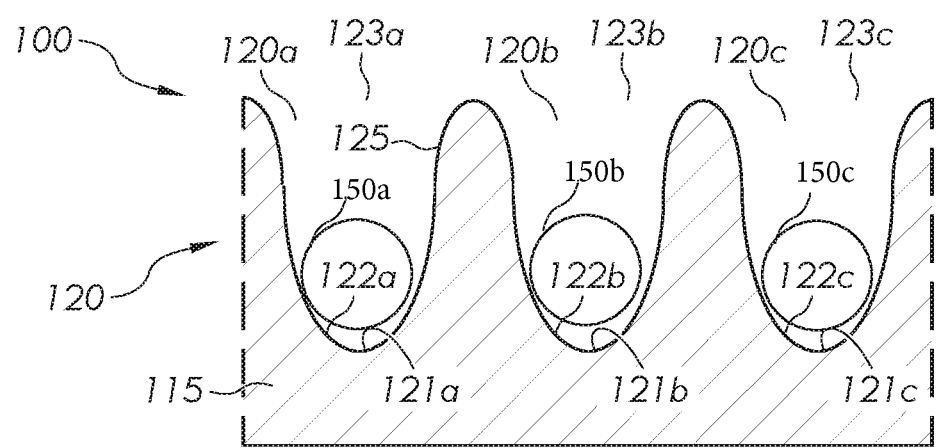
FIG. 5 illustrates an enlarged schematic representation of an exemplary embodiment of a portion of cell culture vessel taken at view 5 of FIG. 3 including a substrate including a plurality of microcavities including at least one aperture in accordance with embodiments of the disclosure.

FIG. 4 shows an enlarged schematic representation of a portion of the substrate 215 shown in FIG. 3, having a microcavity array 115. Additionally, FIG. 5 shows a cross-sectional view of the portion of the surface shown as 5 in FIG. 3 having a microcavity array 115. As shown in FIGS. 4 and 5, in some embodiments, each microcavity 120 (shown as 120a, 120b, 120c) in the array of microcavities 115 in the top surface 120 of the substrate 216 has an opening 123a, 123b, 123c at the top of each microcavity 120. And, each microcavity 120 in the array of microcavities 115 can include a concave surface 121a, 121b, 121c defining a well 122a, 122b, 122c. Further, each microcavity 120a, 120b, 120c can include a well 122a, 122b, 122c. These structures are present whether the microcavity array is integral to the bottom 108 of the vessel 100 or whether the microcavity array is provided by an insert 215 having a microcavity array 315.

In some embodiments, the substrate 215 can be a polymeric material including, but not limited to, polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers. Additionally, in some embodiments, at least a portion of the well 122a, 122b, 122c defined by the concave surface 121a, 121b, 121c can be coated with an ultra-low binding material, thereby making the at least a portion of the well 122a, 122b, 122c non-adherent to cells. For example, in some embodiments, one or more of per-fluorinated polymers, olefins, agarose, non-ionic hydrogels such as polyacrylamides, polyethers such as polyethyleneoxide, polyols such as polyvinylalcohol or mixtures thereof can be applied to at least a portion of the well 122a, 122b, 122c defined by the concave surface 121a, 121b, 121c.

Moreover, in some embodiments, each microcavity 120a, 120b, 120c of the plurality of microcavities 120 can include a variety of features and variations of those features without departing from the scope of the disclosure. For example, in some embodiments the plurality of microcavities 120 can be arranged in an array including a linear array (shown), a diagonal array, a rectangular array, a circular array, a radial array, a hexagonal close-packed arrangement, etc. Additionally, in some embodiments, the opening 123a, 123b, 123c can include a variety of shapes. In some embodiments, the opening 123a, 123b, 123c can include one or more of a circle, an oval, a rectangle, a quadrilateral, a hexagon, and other polygonal shapes. Additionally, in some embodiments, the opening 123a, 123b, 123c can include a dimension (e.g., diameter, width, diagonal of a square or rectangle, etc.) from about 100 microns (μm) to about 5000 μm. For example, in some embodiments, the opening 123a, 123b, 123c can include a dimension of 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1500 μm, 2000 μm, 2500 μm, 3000 μm, 3500 μm, 4000 μm, 4500 μm, 5000 μm, and any dimension or ranges of dimensions encompassed within the range of from about 100 μm to about 5000 μm.

In some embodiments, the well 122a, 122b, 122c defined by the concave surface 121a, 121b, 121c can be any shape. In some embodiments, the well 122a, 122b, 122c defined by the concave surface 121a, 121b, 121c can include one or more of a circular, elliptical, parabolic, hyperbolic, chevron, sloped, or other cross-sectional profile shape. Additionally, in some embodiments, a depth of the well 122a, 122b, 122c (e.g., depth from a plane defined by the opening 123a, 123b, 123c to the concave surface 121a, 121b, 121c can include a dimension from about 100 microns (μm) to about 5000 μm. For example, in some embodiments, the depth of the well 122a, 122b, 122c can include a dimension of 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1500 μm, 2000 μm, 2500 μm, 3000 μm, 3500 μm, 4000 μm, 4500 μm, 5000 μm, any dimension or ranges of dimensions encompassed within the range of from about 100 μm to about 5000 μm.

FIG. 5 illustrates that in some embodiments, three-dimensional cells 150 (e.g., spheroids, organoids 150a, 150b, 150c) that can be cultured in at least one microcavity 120a, 120b, 120c of the plurality of microcavities 120 can include a dimension (e.g., diameter) of from about 50 μm to about 5000 μm, and any dimension or ranges of dimensions encompassed within the range of from about 50 μm to about 5000 μm. In some embodiments, dimensions greater than or less than the explicit dimensions disclosed can be provided and, therefore, unless otherwise noted, dimensions greater than or less than the explicit dimensions disclosed are considered to be within the scope of the disclosure. For example, in some embodiments, one or more dimensions of the opening 123a, 123b, 123c, the depth of the well 122a, 122b, 122c, and the dimension of the three-dimensional cells 150 (e.g., spheroids 150a, 150b, 150c) can be greater than or less than the explicit dimensions disclosed without departing from the scope of the disclosure.

Figure 6:
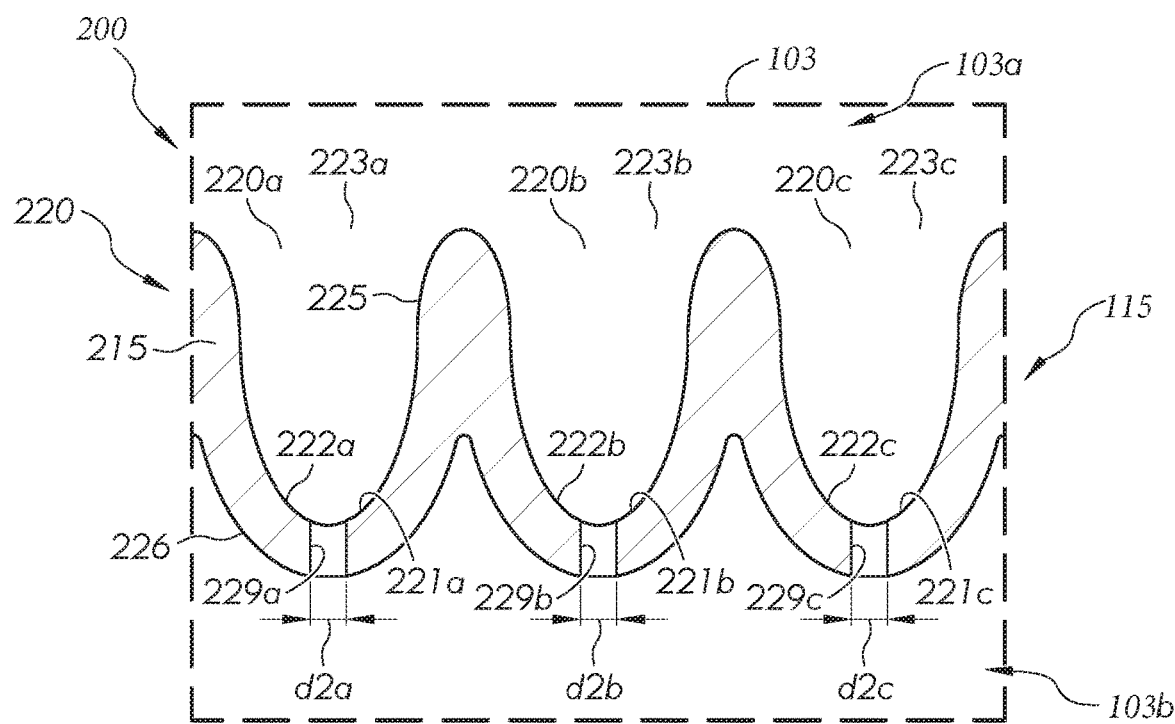
FIG. 6 shows an alternative embodiment of the portion of the cell culture vessel portion of cell culture vessel taken at view 5 of FIG. 3 including a substrate including a plurality of microcavities and a layer of porous material in accordance with embodiments of the disclosure

As shown in FIG. 6, which illustrates an enlarged schematic representation of another exemplary embodiment of a microcavity array 220 in a vessel 200, in some embodiments, each microcavity 220a, 220b, 220c of the plurality of microcavities 220 can include a concave surface 221a, 221b, 221c defining a well 222a, 222b, 222c and an opening 223a, 223b, 223c defining a path from the first region 103a (as shown in FIG. 3) into the well 222a, 222b, 222c. That is, liquid media and cells can enter the microcavities through the openings 223a, 223b, 223c in the top of each microcavity 220a, 220b, 220c. In some embodiments, the concave surface 221a, 221b, 221c of each microcavity 220a, 220b, 220c can include at least one aperture 229a, 229b, 229c including a dimension d2a, d2b, d2c less than or equal to about 15 microns. The at least one aperture 229a, 229b, 229c can extend from a top side 225 of the substrate 215 through the substrate 215 to a bottom side 226 of the substrate 215 and can define a path from the well 222a, 222b, 222c to the second region 103b. For example, in some embodiments, a dimension d2a, d2b, d2c less than or equal to about 15 microns (e.g., 5-15 microns, 5-10 microns, 10-15 microns, 5 microns, and all ranges and subranges therebetween) can provide one or more apertures 229a, 229b, 229c through which gas can pass and through which liquid and cells cannot pass. In some embodiments, each microcavity 220a, 220b, 220c can include a plurality of apertures (not shown). Additionally, the apertures 229a, 229b, 229c can include a profile including one or more of a circle, an oval, a rectangle, or other quadrilaterals. Likewise, in some embodiments, the apertures 229a, 229b, 229c can include a dimension d2a, d2b, d2c (e.g., diameter, width, diagonal of a square or rectangle) less than or equal to about 15 microns.

In some embodiments, the apertures 229a, 229b, 229c can be formed by operation of, for example, laser drilling or laser ablation, machining, manufacturing, forming, or other technique to provide the apertures 229a, 229b, 229c in the microcavities 220a, 220b, 220c of the substrate 215. Thus, in some embodiments, providing the microcavity 220a, 220b, 220c with at least one aperture 229a, 229b, 229c can prevent gas from becoming entrapped in the microcavities 220a, 220b, 220c when a solution media (e.g., liquid containing cells) is deposited in the microcavities 220a, 220b, 220c. Additionally, because the dimension d2a, d2b, d2c is less than or equal to about 15 microns, while gas can pass through the apertures 229a, 229b, 229c, the liquid and cells suspended in the liquid would not pass through the apertures 229a, 229b, 229c without applied force as it is considered that the liquid and the cells (taking into account surface tension of the liquid, in some embodiments) include dimensions greater than or equal to about 15 microns. Further, as compared to a drop-style or hanging cell culture, where cells fall through a hole formed in the bottom of a well and are suspended by surface tension below the profile of the well and are prone to falling away from the well in their suspended droplet of liquid, it is to be understood that features of the disclosure permit containment and culturing of the cells within the well 222a, 222b, 222c, while permitting the passing of gas through the apertures 229a, 229b, 229c, and do not permit cells or spheroids to pass through the apertures 229a, 229b, 229c.

Figure 7:
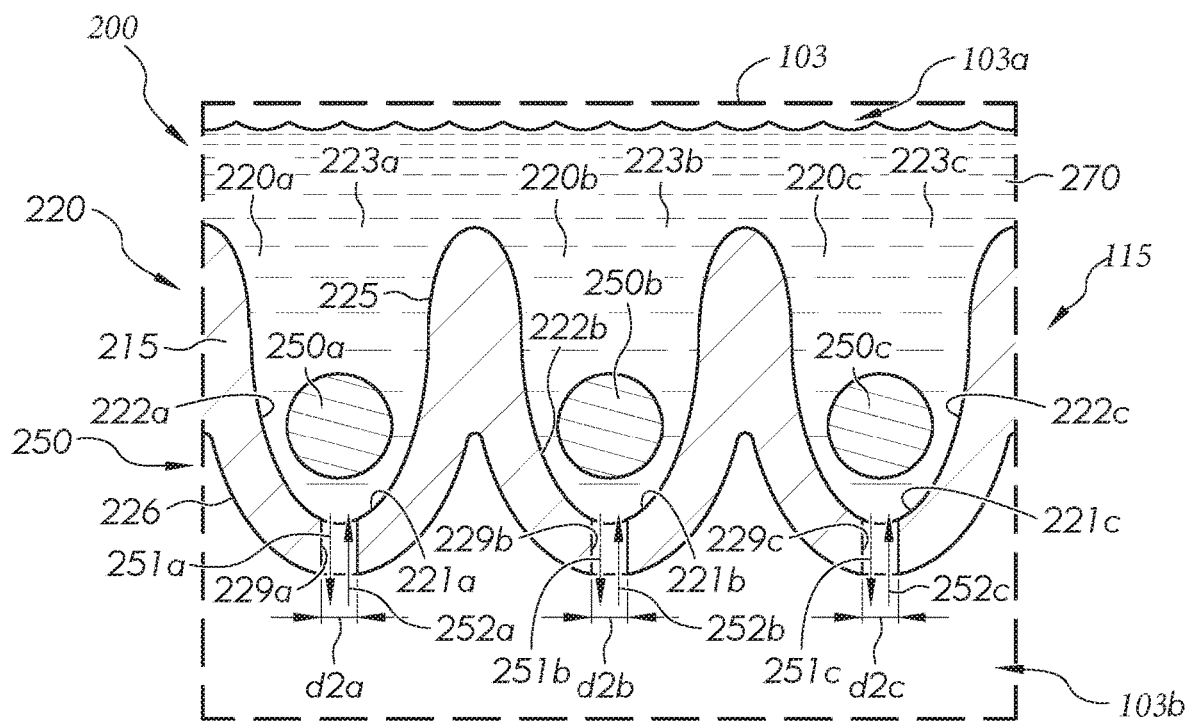
FIG. 7 shows a method of culturing cells in at least one microcavity of the plurality of microcavities including at least one aperture of the substrate of the portion of the cell culture vessel in accordance with embodiments of the disclosure.

For example, as shown in FIG. 7, in some embodiments, a method of culturing cells in the cell culture vessel 200 can include introducing liquid, containing cells into the microcavities 220a, 220b, 220c. As the microcavities 220a, 220b, 220c fill with liquid, gas passes down through the at least one aperture 229a, 229b, 229c in the concave surface 221a, 221ba, 221c of at least one microcavity 220a, 220b, 220c of the plurality of microcavities 220. Because of the surface tension of media, which contains proteins and other ingredients which lend media a relatively high surface tension, and because of the small size of the microcavities 220a, 220b, 220c, bubble formation is a concern. Bubbles interfere with cell culture. In embodiments, by allowing gas to leave the microcavities as liquid enters the microcavities, bubbles do not form in the microcavities. The method shown in FIG. 7 also includes culturing cells or spheroids 250 (e.g., three-dimensional cell 250a, three-dimensional cell 250b, three-dimensional cell 250c) in the at least one microcavity 220a, 220b, 220c. For example, as represented by arrows 251a, 251b, 251c, gas can pass from the at least one microcavity 220a, 220b, 220c through the at least one aperture 229a, 229b, 229c in the concave surface 221a, 221b, 221c of the at least one microcavity 220a, 220b, 220c into the second region 103b of the cell culture chamber 103. Alternatively, as represented by arrows 252a, 252b, 252c gas can pass from the second region 103b of the cell culture chamber 103 through the at least one aperture 229a, 229b, 229c in the concave surface 221a, 221b, 221c of the at least one microcavity 220a, 220b, 220c into the at least one microcavity 220a, 220b, 220c.

In some embodiments, liquid 270 including cells 250a, 250b, 250c can be contained and cultured in the microcavities 220a, 220b, 220c while gas can pass through the apertures 229a, 229b, 229c. Allowing gas to pass through the apertures 229a, 229b, 229c while containing liquid 270 and culturing cells 250a, 250b, 250c in the at least one microcavity 220a, 220b, 220c, not only prevents gas entrapment (e.g., during initial filling of the at least one microcavity 220a, 220b, 220c with liquid 270) but also permits the passage of gas into and out of the at least one microcavity 220a, 220b, 220c during culturing. For example, in some embodiments, gas produced by the cells 250a, 250b, 250c as a byproduct of cell culturing can be removed from the microcavities 220a, 220b, 220c by passing through the apertures 229a, 229b, 229c while culturing the cells 250a, 250b, 250c. Similarly, in some embodiments, gas to aid in cell culturing of the cells 250a, 250b, 250c can be added to the microcavities 220a, 220b, 220c by passing through the apertures 229a, 229b, 229c while culturing the cells 250a, 250b, 250c.

Figure 8:
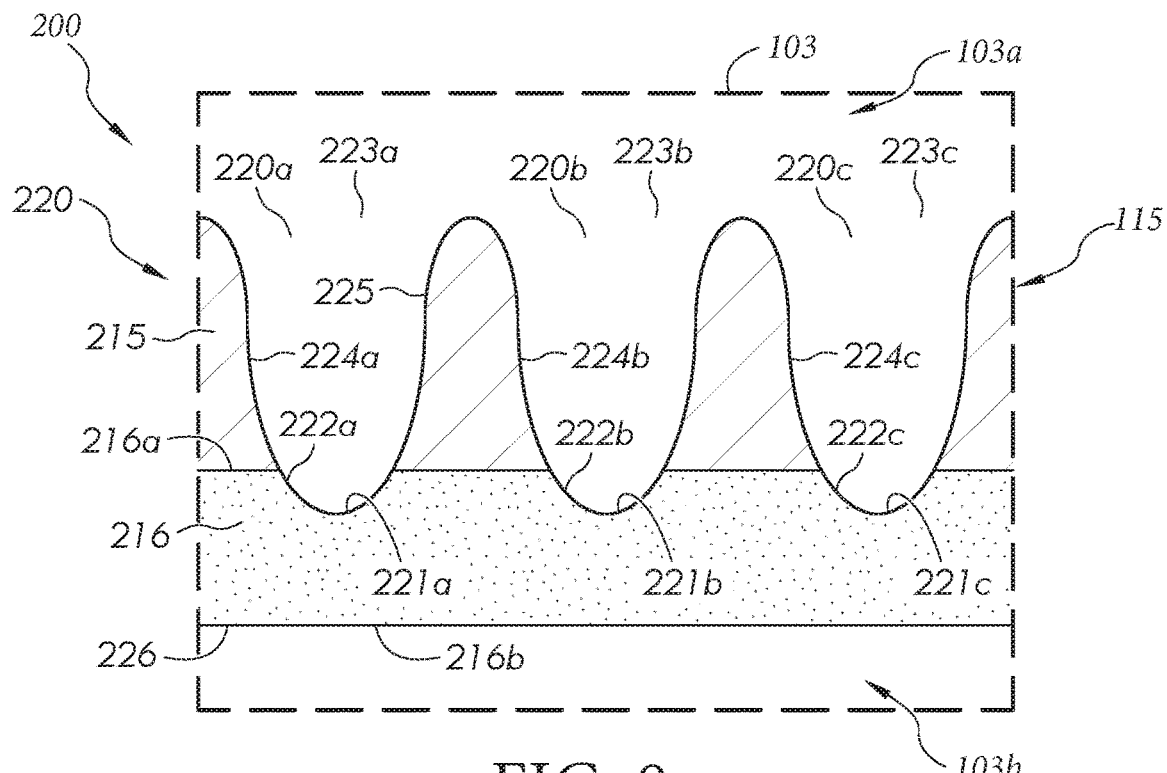
FIG. 8 shows an alternative embodiment of the portion of the cell culture vessel portion of cell culture vessel taken at view 5 of FIG. 3 including a substrate having a plurality of microcavities and a layer of porous material in accordance with embodiments of the disclosure.

Alternatively, as shown in FIGS. 8-11, in some embodiments, the substrate 215 can include a layer of porous material 216. In some embodiments, each microcavity 220a, 220b, 220c of the plurality of microcavities 220 can include a microcavity sidewall surface 224a, 224b, 224c extending from the opening 223a, 223b, 223c to the concave surface 221a, 221b, 221c. As shown in FIG. 8, in some embodiments, a first side 216a of the layer of porous material 216 can define at least a portion of the concave surface 221a, 221b, 221c of each microcavity 220a, 220b, 220c of the plurality of microcavities 220, and a second side 216b of the layer of porous material 216 can face the second region 103b. In some embodiments, the first side 216a of the layer of porous material 216 can define the entirety of the concave surface 221a, 221b, 221c of each microcavity 220a, 220b, 220c of the plurality of microcavities 220.

Figure 9:
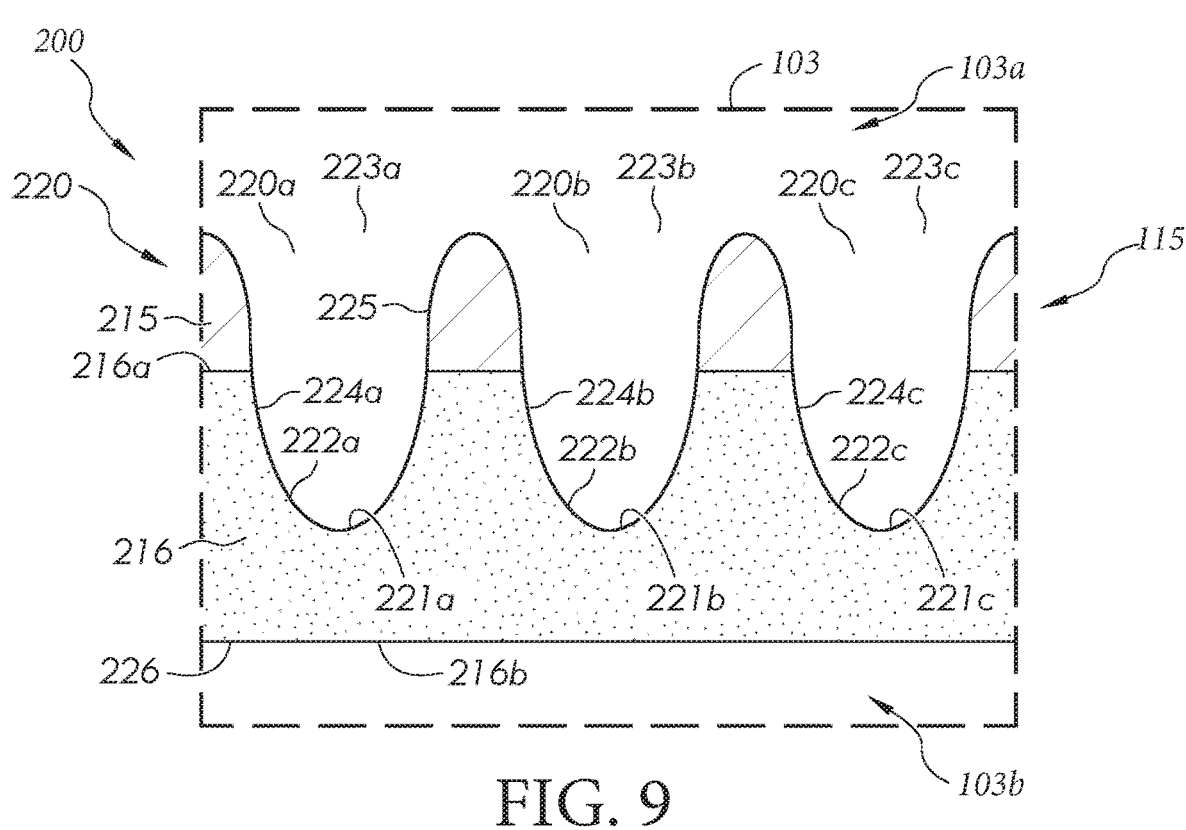
FIG. 9 shows an alternative embodiment of the portion of the cell culture vessel including a substrate having a plurality of microcavities and a layer of porous material in accordance with embodiments of the disclosure.
Figure 10:
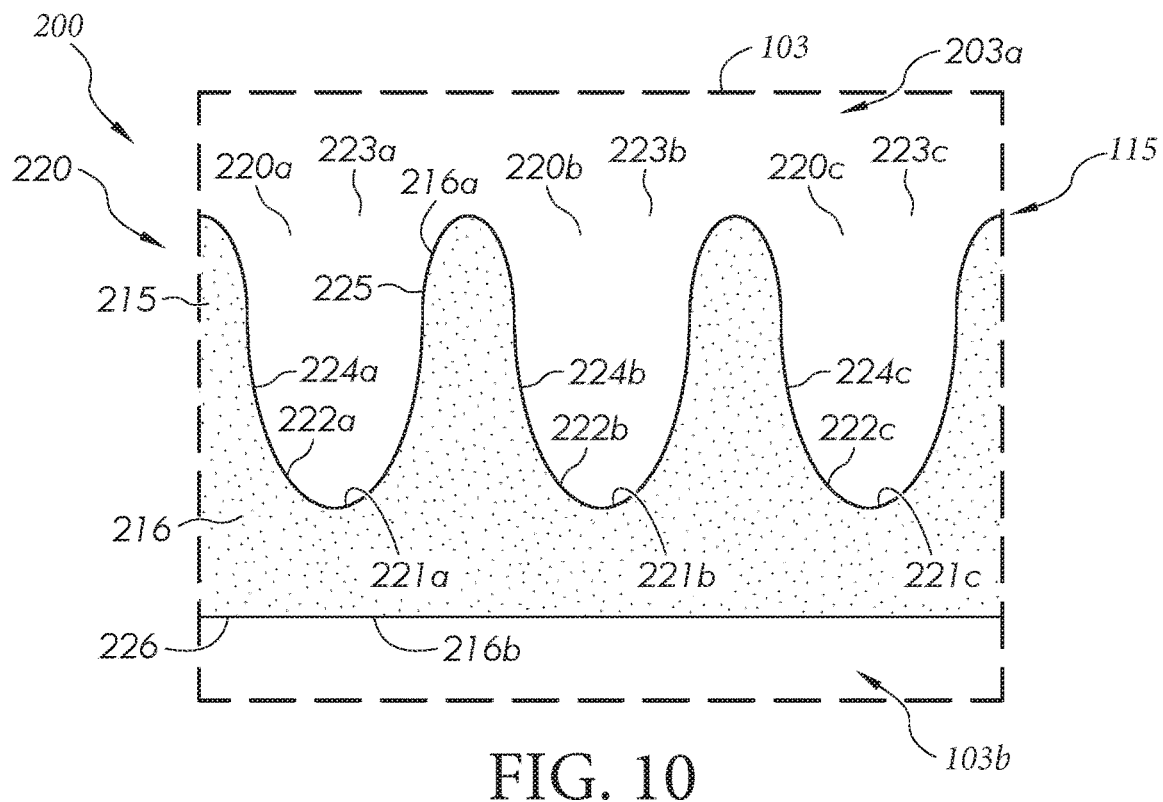
FIG. 10 shows an alternative embodiment of the portion of the cell culture vessel including a substrate having a plurality of microcavities and a layer of porous material in accordance with embodiments of the disclosure

As shown in FIG. 9, in some embodiments, the first side 216a of the layer of porous material 216 can define at least a portion of the sidewall surface 224a, 224b, 224c of each microcavity 220a, 220b, 220c of the plurality of microcavities 220. In some embodiments, the first side 216a of the layer of porous material 216 can define the entirety of the sidewall surface 224a, 224b, 224c of each microcavity 220a, 220b, 220c of the plurality of microcavities 220. As shown in FIG. 10, the layer of porous material 216 can define the entirety of the substrate 215, where the first side 216a of the layer of porous material defines the first side 225 of the substrate 215 and the second side 216b of the layer of porous material defines the second side 226 of the substrate 215.

Figure 11:
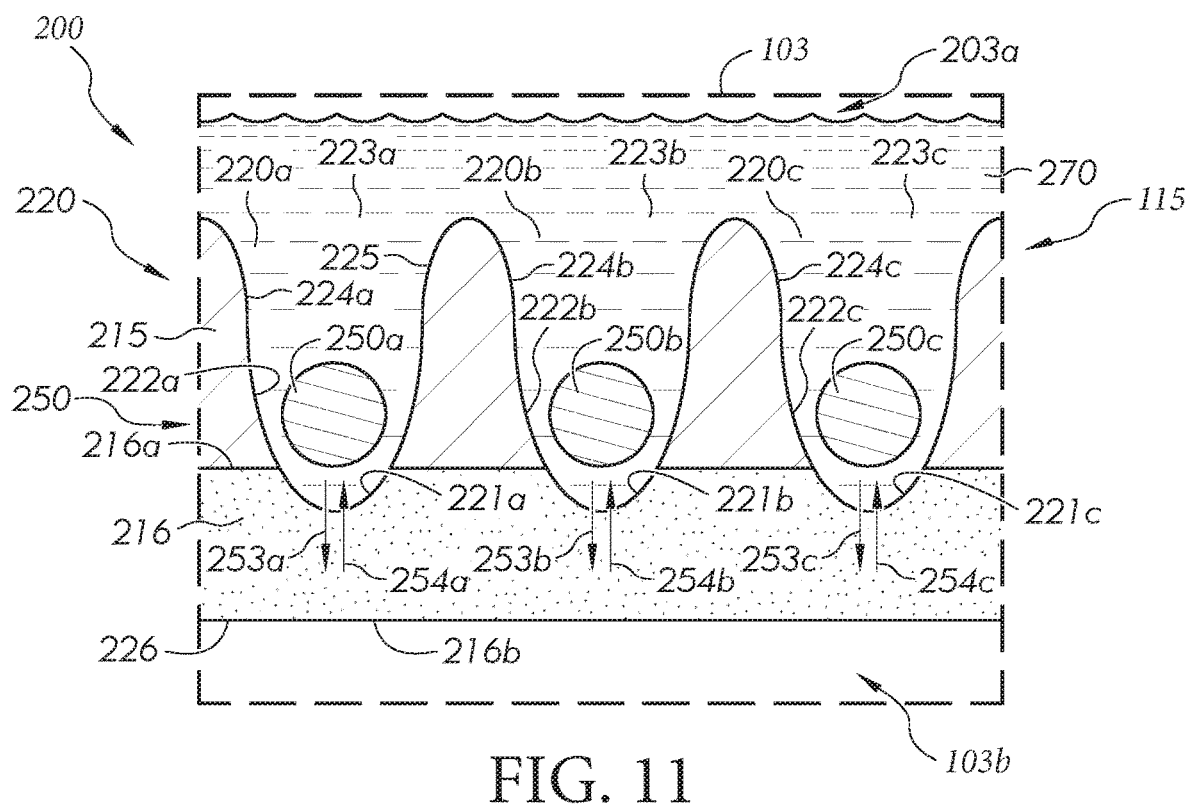
FIG. 11 shows a method of culturing cells in at least one microcavity of the plurality of microcavities of the portion of the substrate including a plurality of microcavities and a layer of porous material in accordance with embodiments of the disclosure.
Figure 12:
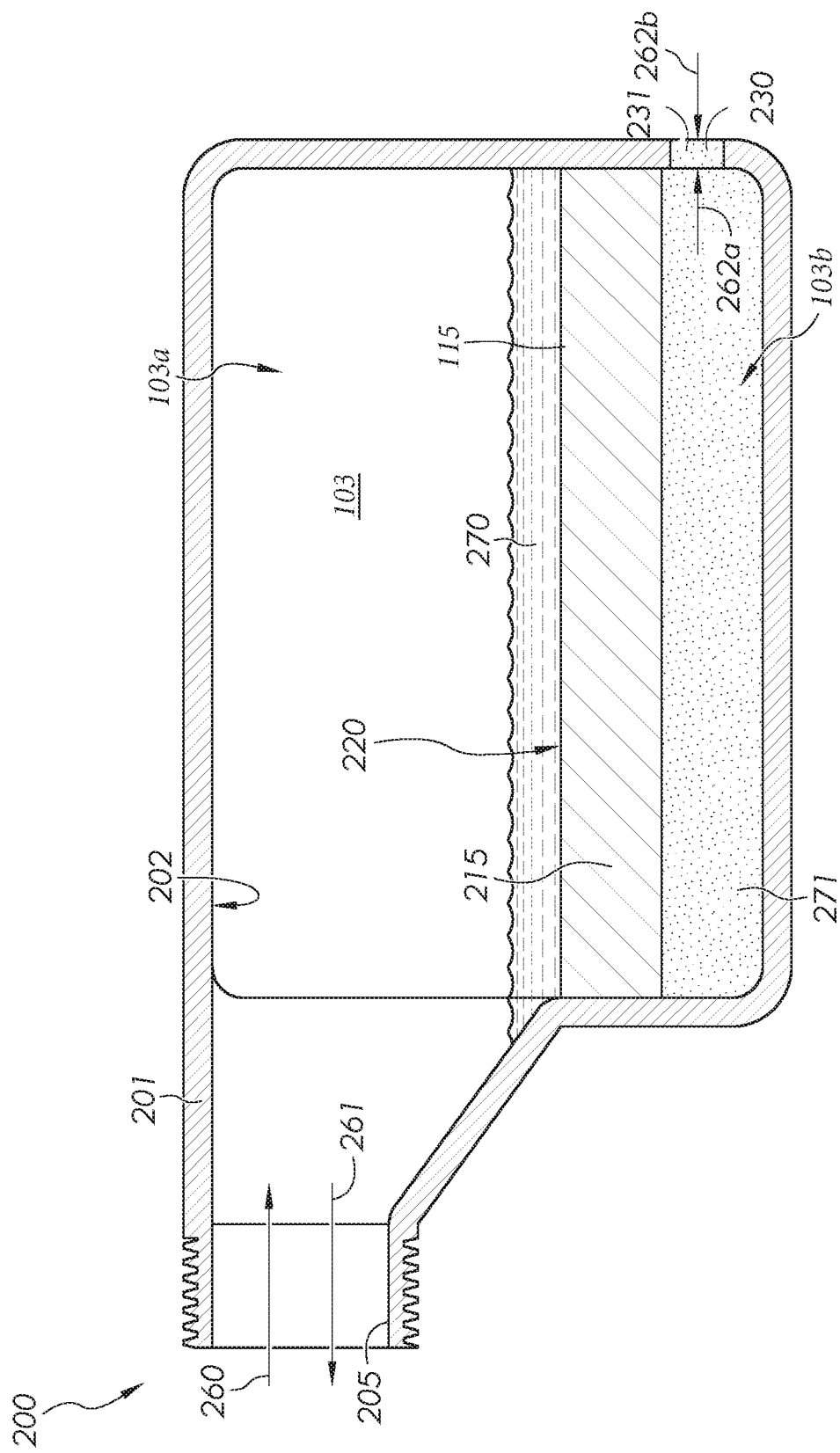
FIG. 12 shows an alternative embodiment of the cross-sectional view of the cell culture vessel including a port and a gas-permeable filter in accordance with embodiments of the disclosure.

As shown in FIG. 11, in some embodiments, a method of culturing cells 250 in the cell culture vessel 100 can include passing gas into the at least a portion of the concave surface 221a, 221b, 221c defined by the first side 216a of the layer of porous material 216 of at least one microcavity 220a, 220b, 220c of the plurality of microcavities 220 and culturing cells in the at least one microcavity 220a, 220b, 220c. For example, as represented by arrows 253a, 253b, 253c, gas can pass from the at least one microcavity 220a, 220b, 220c into the layer of porous material 216, and then, the gas can pass from the layer of porous material 216 into the second region 103b of the cell culture chamber 103. Alternatively, gas can pass from the second region 103b of the cell culture chamber 103 into the layer of porous material 216, and then, as represented by arrow 254a, 254b, 254c gas can pass from the layer of porous material 216 into the at least one microcavity 220a, 220b, 220c.

In some embodiments, liquid 270 including cells 250a, 250b, 250c can be contained and cultured in the microcavities 220a, 220b, 220c while gas can pass through the layer of porous material 216. Allowing gas to pass through the layer of porous material 216 while containing liquid 270 and culturing cells 250a, 250b, 250c in the at least one microcavity 220a, 220b, 220c, not only prevents gas entrapment (e.g., during initial filling of the at least one microcavity 220a, 220b, 220c with liquid 270) but also permits the passage of gas into and out of the layer of porous material 216 during culturing. For example, in some embodiments, gas produced by the cells 250a, 250b, 250c as a byproduct of cell culturing can be removed from the microcavities 220a, 220b, 220c by passing through the layer of porous material 216 while culturing the cells 250a, 250b, 250c. Similarly, in some embodiments, gas to aid in cell culturing of the cells 250a, 250b, 250c can be added to the microcavities 220a, 220b, 220c by passing through the layer of porous material 216 while culturing the cells 250a, 250b, 250c.

Additionally, as shown in FIGS. 12-15, which show additional exemplary embodiments of the cross-sectional view of a vessel 200, a method of culturing cells 250 in the cell culture vessel 200 can include passing liquid 270 through the first aperture 205, and culturing cells 250a, 250b, 250c in at least one microcavity 220a, 220b, 220c of the plurality of microcavities 220 (See FIG. 5 and FIG. 7). Unless otherwise noted, the substrate 215 described with respect to features of FIGS. 12-15 can include one or more features of the substrate 215 shown in FIG. 6 and FIG. 7 including the apertures 229a, 229b, 229c as well as one or more features of the substrate 215 shown in FIGS. 8-11. In some embodiments, as represented by arrow 260, the method can include passing liquid 270 through the first aperture 205 from outside the vessel 200 into the first region 103a.

As shown in FIG. 10, in some embodiments, the vessel 200 can include a port 230 extending through the wall 101 in fluid communication with the second region 103b. In embodiments, the port 231 may include gas-permeable material 231. In some embodiments, the method can include passing gas 271 through the gas-permeable material 231 of the port 230, and culturing cells in the plurality of microcavities 220. In embodiments, the gas permeable material 231 may be a gas permeable filter. For example, as represented by arrow 262a, gas 271 can pass from the second region 103b into the gas-permeable material 231 of the port 230, and then, for example, gas can pass from the gas-permeable material 231 to outside the vessel 200. Likewise, as represented by arrow 262b, gas can pass from outside the vessel 200 through the gas-permeable material 231 of the port 230, and then, for example, gas can pass from the gas-permeable filter 231 in to the second region 103b. Providing the second region 103b with a port 230 including a gas-permeable filter 231 can allow gas exchange between, for example, the second region 103b and the environment outside the vessel 200, thereby preventing pressurization (e.g., over-pressurization) of gas 271 in the second region 103b of the cell culture chamber 103 of the vessel 200. Additionally, in some embodiments, gas produced by the cells as a byproduct of cell culturing can be removed from the cell culture chamber 103 (e.g., second region 103b) by passing through the port 230 while culturing the cells. Similarly, in some embodiments, gas to aid in cell culturing of the cells can be added to the cell culture chamber 103 (e.g., second region 103b) by passing through the port 230 while culturing the cells 250a, 250b, 250c.

Figure 13:
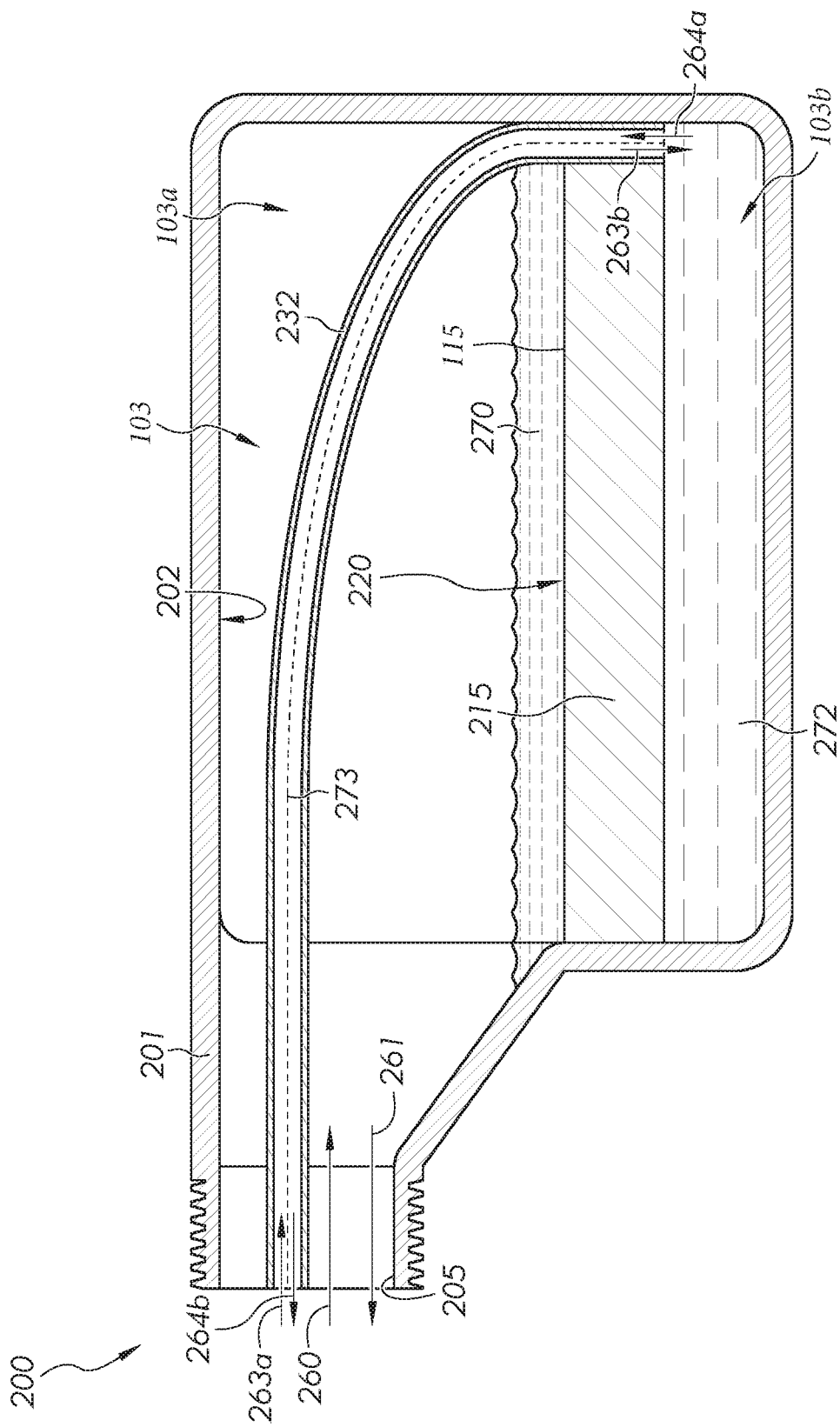
FIG. 13 shows an alternative embodiment of the cross-sectional view of the cell culture vessel including a conduit connecting a first aperture to the second region in accordance with embodiments of the disclosure.

As shown in FIG. 13, in some embodiments, the vessel 200 can include a conduit 232 connecting the first aperture 205 to the second region 103b. For example, in some embodiments, the conduit 232 can include tubing positioned in the cell culture chamber 103 defining a path 273 that is in fluid communication with the first aperture 205 and the second region 103b. In some embodiments, the conduit 232 can provide fluid communication along the path 273 between the outside of the vessel 200 (e.g., via the first aperture 205) and the second region 103b. In some embodiments, the method can include passing liquid 272 through the conduit 232 connecting the first aperture 205 to the second region 103b, and culturing cells in the plurality of microcavities 220. For example, as represented by arrow 263a, liquid 272 can pass from outside the vessel 200 into the conduit 232, along the path 273, and then, as represented by arrow 263b, the liquid 272 can pass from the conduit 232 into the second region 103b. In addition or alternatively, as represented by arrow 264a, liquid 272 can pass from the second region 103b into the conduit 232, along the path 273, and then, as represented by arrow 264b, the liquid 272 can pass from the conduit 232 to outside the vessel 200. In addition, liquid can be introduced into the first region 103a as shown by arrow 260 through the first aperture 205 and removed from the first region 103a as shown by arrow 261.

Figure 14:
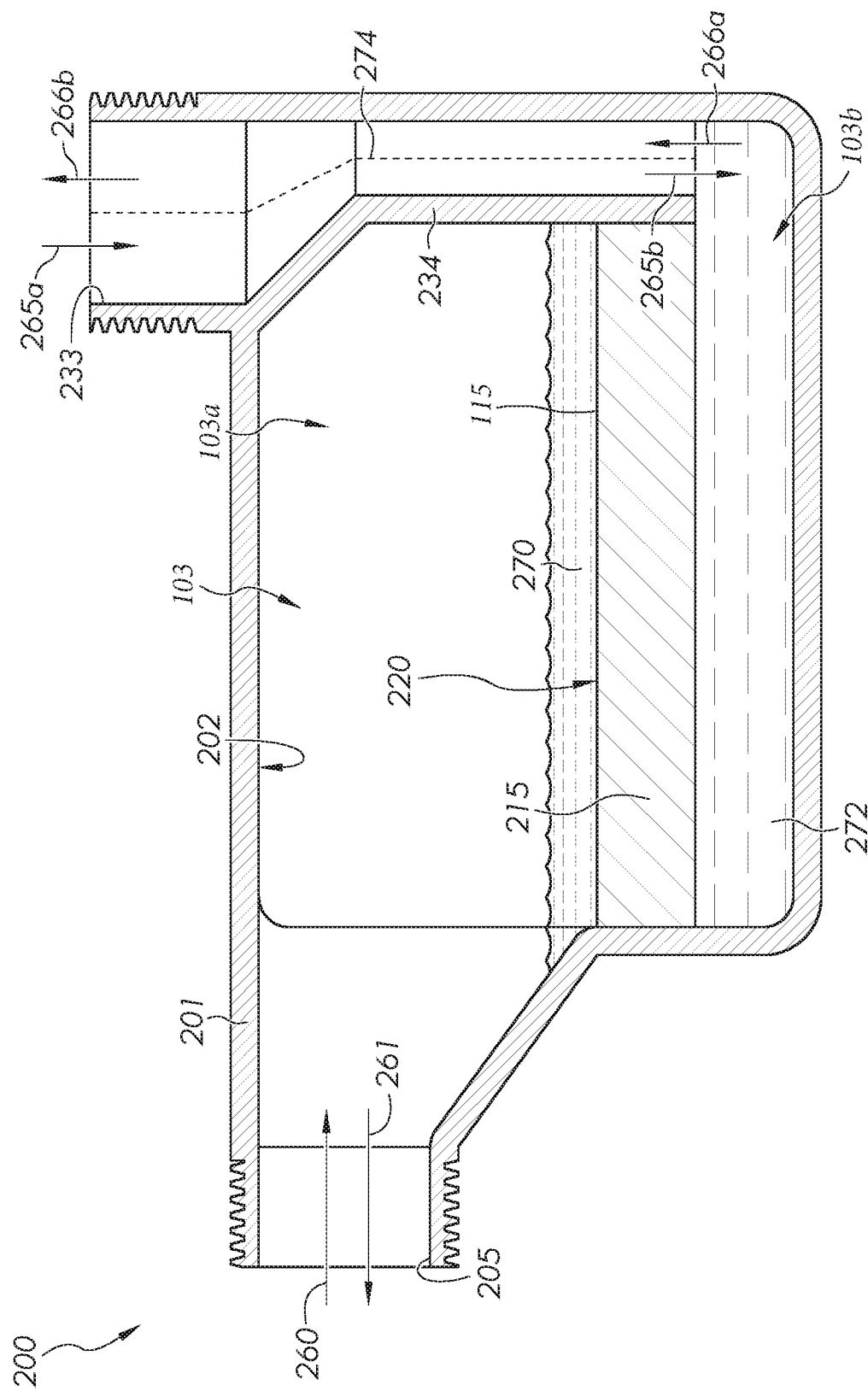
FIG. 14 shows an alternative embodiment of the cross-sectional view of the cell culture vessel including a second aperture and a conduit connecting the second aperture to the second region in accordance with embodiments of the disclosure.

As shown in FIG. 14, in some embodiments, the vessel 200 can include a second aperture 233 extending through the wall 101 in fluid communication with the second region 103b. Additionally, in some embodiments, the vessel 200 can include a conduit 234 connecting the second aperture 233 to the second region 103b. For example, at least one of the second aperture 233 and the conduit 234 can define a path 274 that is in fluid communication with the second aperture 233 and the second region 103b. In some embodiments, the conduit 234 can provide fluid communication along the path 274 between the outside of the vessel 200 (e.g., via the second aperture 233) and the second region 103b. Additionally, in some embodiments, the second aperture 233 can include a cap (not shown, See FIG. 1 and FIG. 2) oriented to cover the second aperture 233 to seal or block the second aperture 233, thereby obstructing a path into the cell culture chamber 103 from outside the vessel 200 through the second aperture 233. In some embodiments, the cap (not shown) of the second aperture 233 can be similar to or the same as the cap 104 of the aperture 105 discussed above with respect to the cell culture vessel 200. In some embodiments, the method can include passing liquid 272 through the second aperture 233 and through the conduit 234, and culturing cells in at least one microcavity 220a, 220b, 220c of the plurality of microcavities 220. For example, as represented by arrow 265a, liquid 272 can pass from outside the vessel 200 into the second aperture 233 and the conduit 234, along the path 274, and then, as represented by arrow 265b, the liquid 272 can pass from the conduit 234 into the second region 103b. In addition or alternatively, as represented by arrow 266a, liquid 272 can pass from the second region 103b into the conduit 234, along the path 274, and then, as represented by arrow 266b, the liquid 272 can pass from the second aperture 233 to outside the vessel 200. In addition, liquid can be introduced into the first region 103a as shown by arrow 260 through the first aperture 205 and removed from the first region 103a as shown by arrow 261.

Turning back to FIG. 13, providing the conduit 232 can allow liquid 272 to be added to or removed from the second region 103b without disturbing the first region 103a of the cell culture chamber 103, and therefore, without disturbing (e.g., dislodging, dislocating, damaging) one or more cells 250a, 250b, 250c of the plurality of cells 250 being cultured in the microcavities 220a, 220b, 220c of the plurality of microcavities 220 of the substrate 215. Likewise, referring to FIG. 14, providing the second aperture 233 and the conduit 234 can allow liquid 272 to be added to or removed from the second region 103b without disturbing the first region 103a of the cell culture chamber 103, and therefore, without disturbing (e.g., dislodging, dislocating, damaging) one or more cells 250a, 250b, 250c of the plurality of cells 250 being cultured in the microcavities 220a, 220b, 220c of the plurality of microcavities 220 of the substrate 215. Additionally, providing liquid 272 in the second region 103b can permit diffusion of nutrients and waste to and from the cells 250a, 250b, 250c through the substrate 215, further reducing or eliminating the possibility of disturbing one or more cells 250a, 250b, 250c being cultured in the microcavities 220a, 220b, 220c. Moreover, providing liquid 272 in the second region 103b, in some embodiments, a rate of gas exchange to and from the cells 250a, 250b, 250c can be selected and controlled based at least on, for example, a height (e.g., head height) of the liquid 270 in the first region 103a. For example, in some embodiments, the resistance of the liquid 270 to gas diffusion through the liquid 270 can be based on a height of the liquid 270 relative to one or more features of the substrate 215. Thus, by providing liquid 272 in the second region 103b and selecting a particular height of liquid 270 in the first region 103a, in some embodiments, the rate of gas diffusion through the liquid 270 can be controlled and improved control over the cell culturing process can be achieved.

Further, when the microcavity array 220 has the features illustrated in FIGS. 6 and 7 (wells with openings) and FIGS. 8-11 (porous material) gas and liquid can pass from the second region 103b to the microcavities 220 through either the well openings or the porous material 216.

Figure 15:
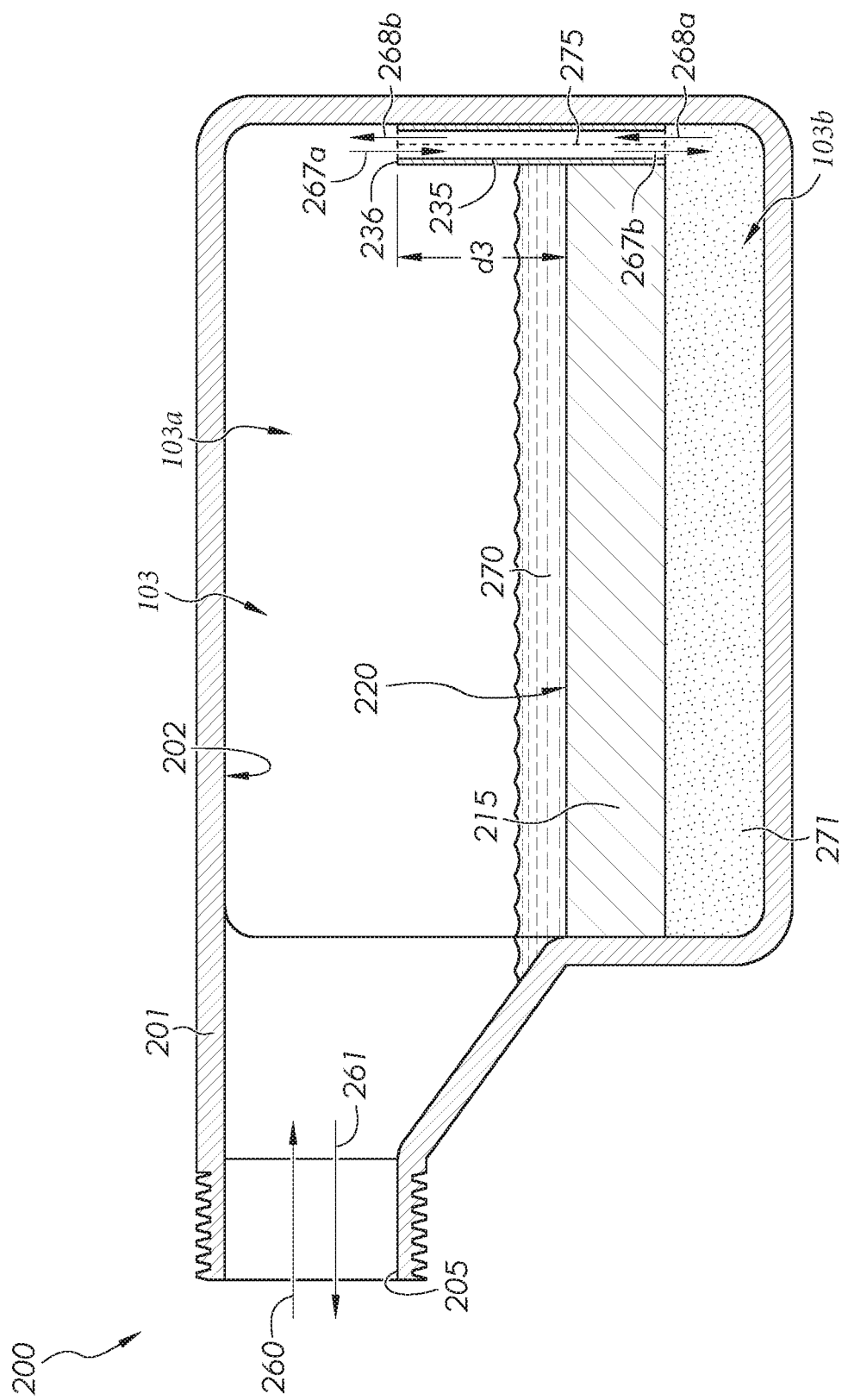
FIG. 15 shows an alternative embodiment of the cross-sectional view of the cell culture vessel including a conduit connecting the first region to the second region in accordance with embodiments of the disclosure.

As shown in FIG. 15 in some embodiments, the vessel 200 can include a conduit 235 connecting the first region 103a to the second region 103b. For example, the conduit 235 can define a path 275 that is in fluid communication with the first region 103a and the second region 103b. In some embodiments, the conduit 235 can provide fluid communication along the path 275 between the first region 103a and the second region 103b. Additionally, in some embodiments, an end 236 of the conduit 237 leading from the first region 103a to the second region 103b can be positioned in the first region 103a spaced (e.g., distance "d3") from the opening 223a, 223b, 223c of each microcavity 220a, 220b, 220c of the plurality of microcavities 220. In some embodiments, the method can include passing gas 271 through the conduit 235 connecting the first region 103a to the second region 103b, and culturing cells in at least one microcavity 220a, 220b, 220c of the plurality of microcavities 220. For example, as represented by arrow 267a, gas 271 can pass from the first region 103a into the conduit 235, along the path 275, and then, as represented by arrow 267b, the gas 271 can pass from the conduit 235 into the second region 103b. In addition or alternatively, as represented by arrow 268a, gas 271 can pass from the second region 103b into the conduit 235, along the path 275, and then, as represented by arrow

268b, the gas 271 can pass from the conduit 235 to the first region 103a. In addition, liquid can be introduced into the first region 103a as shown by arrow 260 through the first aperture 205 and removed from the first region 103a as shown by arrow 261.

Providing the vessel 200 with a conduit 235 can allow gas exchange between, for example, the first region 103a and the second region 103b, thereby preventing pressurization (e.g., over-pressurization) of gas 271 in the second region 103b of the cell culture chamber 103 of the vessel 100. Additionally, in some embodiments, gas produced by the cells 250a, 250b, 250c as a byproduct of cell culturing can be removed from the second region 103b by passing through the conduit 235 into the first region 103a while culturing the cells 250a, 250b, 250c. Similarly, in some embodiments, gas to aid in cell culturing of the cells 250a, 250b, 250c can be added to the second region 103b by passing from the first region 103a through the conduit 235 and into the second region 103b while culturing the cells 250a, 250b, 250c. Additionally, by spacing the end 236 of the conduit 235 leading from the first region 103a to the second region 103b a distance "d3" from the opening 223a, 223b, 223c of each microcavity 220a, 220b, 220c of the plurality of microcavities 220, liquid 270 can be contained within the first region 103a without flowing, splashing, or entering the end 236 of the conduit 235 and flowing into the second region 103b that contains gas 271.

Throughout the disclosure, the terms "material", "liquid", and "gas" can be used to describe properties of a material employed when, for example, culturing cells in the cell culture vessel. Unless otherwise noted, for purposes of the disclosure, "material" can include fluid material (e.g., liquid or gas). Additionally, material can include a culture solution or media including a liquid including solid particles (e.g., cells) suspended in the liquid. Unless otherwise noted, for purposes of the disclosure, "liquid" can include cleaning or rinsing solutions, aqueous solutions, or other liquid that can be added to or removed from the vessel to, for example, clean the cell culture chamber, sterilize one or more features of the substrate and the vessel, prepare the substrate for cellular growth and other uses of liquid. Additionally, liquid can include a culture solution or media including a liquid including solid particles (e.g., cells) suspended in the liquid. Unless otherwise noted, for purposes of the disclosure, "gas" can include air, filtered or treated air, or other gases.

Throughout the disclosure, the terms "non-permeable", "gas-permeable", and "porous" can be used to describe properties (e.g., material properties, characteristics, parameters) of one or more features of a substrate.

Unless otherwise noted, for purposes of the disclosure, a "non-permeable" substrate (e.g., material of a non-permeable substrate) is considered to be impermeable to solid, liquid, and gas under normal conditions (e.g., no external influence including but not limited to pressure and force) and, therefore, does not permit the transfer of solid, liquid, or gas in to, through, or out of, the non-permeable substrate under normal conditions. In some embodiments, a non-permeable substrate can form a portion of the wall of the vessel. Additionally, the cell culture chamber of the vessel is considered to be sterile when a non-permeable substrate forms a portion of the wall of the vessel because bacteria, for example, cannot pass through the non-permeable substrate. However, when filling the plurality of microcavities of the substrate with material, gas can become trapped within the microcavity of a non-permeable substrate based on surface tension of the liquid, thereby, in some embodiments, preventing material from filling the microcavities and preventing growth of a spheroid.

Unless otherwise noted, for purposes of the disclosure, a "gas-permeable" substrate (e.g., material of a gas-permeable substrate) is considered to be impermeable to solid and liquid, and permeable to gas under normal conditions. Therefore, a gas-permeable substrate does not permit the transfer of solid and liquid in to, through, or out of, the gas-permeable substrate and does permit the transfer of gas in to, through, or out of, the gas-permeable substrate. In some embodiments, a gas-permeable substrate can form a portion of the wall of the vessel. Additionally, the cell culture chamber of the vessel is considered to be sterile when a gas-permeable substrate forms a portion of the wall of the vessel because bacteria, for example, cannot reasonably pass through the gas-permeable substrate. However, although the substrate is gas-permeable, gas can still become trapped in the microcavity during filling with material because gas-permeation rates through the gas-permeable substrate can be slower than the rate required to displace gas from the cavity under ordinary operating conditions and can therefore take an unacceptably long amount of time to permeate through the substrate. Thus, in some embodiments, slowly filling the microcavities allows the liquid front to enter each microcavity at an angle, thereby displacing gas as the liquid fills the microcavity. In some embodiments, after filling the cavity with liquid, gas can permeate (slowly) through the gas-permeable substrate.

Unless otherwise noted, for purposes of the disclosure, a "porous" substrate (e.g., material of a porous substrate) is considered to be impermeable to solid and permeable to liquid and gas under normal conditions. Therefore, a porous substrate does not permit the transfer of solid in to, through, or out of, the porous substrate and does permit the transfer of liquid and gas in to, through, or out of, the porous substrate. A porous substrate cannot form a portion of the vessel because bacteria can pass through a porous substrate, thus causing sterility issues in the cell culture chamber. Thus, when using a porous substrate, the substrate must be enclosed (entirely enclosed) in the sterile cell culture chamber of the vessel. During filling of the microcavities with material, however, gas can escape (e.g., pass) through the porous substrate. Thus, filling of the microcavities can be performed rapidly without concern for entrapping gas in the microcavities. In some embodiments, liquid can only pass through the porous substrate with added pressure or physical contact and disturbance of the substrate. Thus, in some embodiments, material including liquid can be contained in the microcavities of the substrate so long as the substrate is not exposed to added pressure or physical contact and disturbance. For example, in some embodiments, the porous substrate can be supported in the cell culture chamber to allow gas to pass through the substrate during filling as well as during culturing and to isolated the substrate from added pressure or physical contact and disturbance from external forces (e.g., outside the cell culture chamber).

A number of aspects of cell culture vessels and methods of culturing cells have been disclosed herein. A summary of some selected aspects is presented below.

In an first aspect, a cell culture vessel is provided, wherein the cell culture vessel has a wall comprising inner surfaces defining a cell culture chamber of the vessel; a substrate of non-porous material positioned in the cell culture chamber between a first region of the cell culture chamber and a second region of the cell culture chamber, the substrate comprising a plurality of microcavities, each microcavity of the plurality of microcavities comprises a concave surface defining a well and an opening defining a path from the first region into the well, the concave surface of each microcavity comprises at least one aperture comprising a dimension less than or equal to about 15 microns defining a path from the well to the second region; and a first aperture extending through the wall in fluid communication with the first region.

In a second aspect, the disclosure provides the features of aspect one, and further provides a port comprising a gas-permeable filter extending through the wall in fluid communication with the second region.

In a third aspect, the disclosure provides the features of aspect one, and further provides a conduit connecting the first aperture to the second region.

In a fourth aspect, the disclosure provides the features of aspect one and further provides a second aperture extending through the wall in fluid communication with the second region.

In a fifth aspect, the disclosure provides the features of aspect four and further provides a conduit connecting the second aperture to the second region.

In a sixth aspect, the disclosure provides the features of aspect one or two and further provides a conduit connecting the first region to the second region.

In a seventh aspect, the disclosure provides the features of aspect six and further provides an end of the conduit leading from the first region to the second region is positioned in the first region spaced from the opening of each microcavity of the plurality of microcavities.

In an eighth aspect, the disclosure provides a method of culturing cells in the cell culture vessel of any one of aspect one through seven, and further provides passing gas through the at least one aperture in the concave surface of at least one microcavity of the plurality of microcavities; and culturing cells in the at least one microcavity.

In a ninth aspect, the disclosure provides a method of culturing cells in any one of aspects one through seven comprising passing liquid through the first aperture; and culturing cells in at least one microcavity of the plurality of microcavities.

In a tenth aspect, the disclosure provides a method of culturing cells in any one of aspects one through seven comprising passing liquid through the first aperture from outside the vessel into the first region; depositing at least a portion of the liquid in at least one microcavity of the plurality of microcavities; and culturing cells in the at least one microcavity of the plurality of microcavities after depositing the at least a portion of the liquid in the at least one microcavity.

In an eleventh aspect, the disclosure provides a method of culturing cells in a cell culture vessel according to aspect two, comprising passing gas into the gas-permeable filter of the port, and culturing cells in at least one microcavity of the plurality of microcavities.

In a twelfth aspect, the disclosure provides a method of culturing cells in a cell culture vessel according to aspect two, comprising passing liquid through the conduit connecting the first aperture to the second region, and culturing cells in at least one microcavity of the plurality of microcavities.

In a thirteenth aspect, the disclosure provides a method of culturing cells in a cell culture vessel according to aspect four comprising passing liquid through the second aperture; and culturing cells in at least one microcavity of the plurality of microcavities.

In a fourteenth aspect, the disclosure provides a method of culturing cells in a cell culture vessel according to aspect five comprising passing liquid through the conduit connecting the second aperture to the second region; and culturing cells in at least one microcavity of the plurality of microcavities.

In a fifteenth aspect, the disclosure provides a method of culturing cells in a cell culture vessel according to aspect six comprising passing gas through the conduit connecting the first region to the second region, and culturing cells in at least one microcavity of the plurality of microcavities.

In a sixteenth aspect, the disclosure provides cell culture vessel having a wall comprising an inner surface defining a cell culture chamber of the vessel; a substrate positioned in the cell culture chamber between a first region of the cell culture chamber and a second region of the cell culture chamber, the substrate comprising a plurality of microcavities and a layer of porous material, each microcavity of the plurality of microcavities comprises a concave surface defining a well and an opening defining a path from the first region into the well, a first side of the layer of porous material defines at least a portion of the concave surface of each microcavity of the plurality of microcavities, and a second side of the layer of porous material faces the second region; and a first aperture extending through the wall in fluid communication with the first region.

In a seventeenth aspect, the disclosure provides the cell culture vessel of aspect sixteen the first side of the layer of porous material defines the entirety of the concave surface of each microcavity of the plurality of microcavities.

In an eighteenth aspect, the disclosure provides the cell culture vessel of aspect sixteen or seventeen each microcavity of the plurality of microcavities comprises a sidewall surface extending from the opening to the concave surface, and the first side of the layer of porous material defines at least a portion of the sidewall surface of each microcavity of the plurality of microcavities.

In a nineteenth aspect, the disclosure provides the cell culture vessel of aspect eighteen the first side of the layer of porous material defines the entirety of the sidewall surface of each microcavity of the plurality of microcavities.

In a twentieth aspect, the disclosure provides the cell culture vessel of any one of aspects sixteen through nineteen the layer of porous material defines the entirety of the substrate.

In a twenty-first aspect the disclosure provides the cell culture vessel of any one of aspect sixteen through twenty comprising a port comprising a gas-permeable filter extending through the wall in fluid communication with the second region.

In a twenty-second aspect, the disclosure provides the cell culture vessel of any one of aspect sixteen through twenty including a conduit connecting the first aperture to the second region.

In a twenty-third aspect, the disclosure provides the cell culture vessel of any one of aspect sixteen through twenty including a second aperture extending through the wall in fluid communication with the second region.

In a twenty-fourth aspect, the disclosure provides the cell culture vessel of twenty-three including a conduit connecting the second aperture to the second region.

In a twenty-fifth aspect, the disclosure provides the cell culture vessel according to any one of aspects sixteen to twenty one including comprising a conduit connecting the first region to the second region.

In a twenty-sixth aspect, the disclosure provides the cell culture vessel according to aspect twenty-fife including an end of the conduit leading from the first region to the second region is positioned in the first region spaced from the opening of each microcavity of the plurality of microcavities.

In a twenty-seventh aspect, the disclosure provides the cell culture vessel of any one of aspects sixteen to twenty-six including passing gas into the at least a portion of the concave surface defined by the first side of the layer of porous material of at least one microcavity of the plurality of microcavities; and culturing cells in the at least one microcavity.

In a twenty-eighth aspect, the disclosure provides a method of culturing cells in the cell culture vessel of any one of aspects sixteen to twenty-six including passing liquid through the first aperture; and culturing cells in at least one microcavity of the plurality of microcavities.

In a twenty-ninth aspect, the disclosure provides a method of culturing cells in the cell culture vessel of any one of aspects sixteen to twenty-six including passing liquid through the first aperture from outside the vessel into the first region; depositing at least a portion of the liquid in at least one microcavity of the plurality of microcavities; and culturing cells in the at least one microcavity of the plurality of microcavities after depositing the at least a portion of the liquid in the at least one microcavity.

In a thirtieth aspect, the disclosure provides a method of of culturing cells in the cell culture vessel of aspect twenty-one passing gas into the gas-permeable filter of the port, and culturing cells in at least one microcavity of the plurality of microcavities.

In a thirty-first aspect, the disclosure provides a method of culturing cells in the cell culture vessel of any aspect twenty-two including passing liquid through the conduit connecting the first aperture to the second region, and culturing cells in at least one microcavity of the plurality of microcavities.

In a thirty-second aspect, the disclosure provides a method of culturing cells in the cell culture vessel of aspects twenty-three including passing liquid through the second aperture; and culturing cells in at least one microcavity of the plurality of microcavities.

In a thirty-third aspect, the disclosure provides a method of culturing cells in the cell culture vessel of aspect twenty-four including passing liquid through the conduit connecting the second aperture to the second region; and culturing cells in at least one microcavity of the plurality of microcavities.

In a thirty-fourth aspect, the disclosure provides a method of culturing cells in the cell culture vessel of any one of aspects twenty-five or twenty-six including passing gas through the conduit connecting the first region to the second region, and culturing cells in at least one microcavity of the plurality of microcavities.

In an embodiment, the disclosure provides, a cell culture vessel includes a substrate including a plurality of microcavities; a wall, the substrate and an inner surface of the wall define a cell culture chamber of the vessel; an aperture extending through the wall in fluid communication with the cell culture chamber; a first portion of the inner surface positioned opposite the aperture along an axis of the vessel, the substrate spans a length of the cell culture chamber that extends along the axis of the vessel; a second portion of the inner surface extending from the aperture to the substrate; and a third portion of the inner surface extending from the first portion to the substrate.

It will be appreciated that the various disclosed embodiments can involve particular features, elements or steps that are described in connection with that particular embodiment. It will also be appreciated that a particular feature, element or step, although described in relation to one particular embodiment, can be interchanged or combined with alternate embodiments in various non-illustrated combinations or permutations.

It is to be understood that, as used herein the terms "the," "a," or "an," mean "at least one," and should not be limited to "only one" unless explicitly indicated to the contrary. Thus, for example, reference to "a component" includes embodiments having two or more such components unless the context clearly indicates otherwise.

Ranges can be expressed herein as from "about" one particular value, and/or to "about" another particular value. When such a range is expressed, embodiments include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments can be disclosed using the transitional phrase "comprising," it is to be understood that alternative embodiments, including those that can be described using the transitional phrases "consisting" or "consisting essentially of," are implied. Thus, for example, implied alternative embodiments to an apparatus that comprises A+B+C include embodiments where an apparatus consists of A+B+C and embodiments where an apparatus consists essentially of A+B+C.

It will be apparent to those skilled in the art that various modifications and variations can be made to the present disclosure without departing from the spirit and scope of the disclosure. Thus, it is intended that the present disclosure cover the modifications and variations of this disclosure provided they come within the scope of the appended claims and their equivalents.

What is claimed is:

1. A cell culture vessel comprising:
a wall comprising inner surfaces defining a cell culture chamber of the vessel;
a substrate of non-porous material positioned in the cell culture chamber between a first region of the cell culture chamber and a second region of the cell culture chamber, the substrate comprising a plurality of microcavities, each microcavity of the plurality of microcavities comprising a concave surface defining a well and an opening defining a path from the first region into the well, the concave surface of each microcavity comprising at least one aperture comprising a dimension less than or equal to about 15 microns defining a path from the well to the second region, wherein the path is not porous to liquid based on surface tension without an applied force and provides for gas-exchange between the second region of the cell culture chamber and the microcavity; and
a first aperture extending through the wall in fluid communication with the first region.

2. The cell culture vessel of claim 1, further comprising a port extending through the wall in fluid communication with the second region, the port comprising a gas-permeable filter.

3. The cell culture vessel of claim 2, further comprising a conduit fluidly connecting the first region to the second region.

4. The cell culture vessel of claim 3, wherein an end of the conduit leading from the first region to the second region is positioned in the first region and spaced from the opening of each microcavity of the plurality of microcavities.

5. A method of culturing cells in the cell culture vessel of claim 4, comprising:
 passing liquid through the first aperture from outside the vessel into the first region;
 depositing at least a portion of the liquid in at least one microcavity of the plurality of microcavities; and
 culturing cells in the at least one microcavity of the plurality of microcavities after depositing the at least a portion of the liquid in the at least one microcavity.

6. A method of culturing cells in the cell culture vessel of claim 3, comprising passing gas through the conduit connecting the first region to the second region, and culturing cells in at least one microcavity of the plurality of microcavities.

7. A method of culturing cells in the cell culture vessel of claim 2, comprising passing gas into the gas-permeable filter of the port, and culturing cells in at least one microcavity of the plurality of microcavities.

8. The cell culture vessel of claim 1, further comprising a conduit connecting the first aperture to the second region.

9. A method of culturing cells in the cell culture vessel of claim 8, comprising passing liquid through the conduit connecting the first aperture to the second region, and culturing cells in at least one microcavity of the plurality of microcavities.

10. The cell culture vessel of claim 1, further comprising a second aperture extending through the wall, wherein the second aperture is in fluid communication with the second region.

11. The cell culture vessel of claim 10, further comprising a conduit fluidly connecting the second aperture to the second region.

12. A method of culturing cells in the cell culture vessel of claim 11, comprising:
 passing liquid through the conduit connecting the second aperture to the second region; and
 culturing cells in at least one microcavity of the plurality of microcavities.

13. A method of culturing cells in the cell culture vessel of claim 10, comprising:
 passing liquid through the second aperture; and
 culturing cells in at least one microcavity of the plurality of microcavities.

14. A method of culturing cells in the cell culture vessel of claim 1, comprising:
 passing gas through the at least one aperture in the concave surface of at least one microcavity of the plurality of microcavities; and
 culturing cells in the at least one microcavity.

15. A method of culturing cells in the cell culture vessel of claim 1, comprising:
 passing liquid through the first aperture; and
 culturing cells in at least one microcavity of the plurality of microcavities.

16. A cell culture vessel comprising:
 a wall comprising an inner surface defining a cell culture chamber of the vessel;
 a substrate positioned in the cell culture chamber between a first region of the cell culture chamber and a second region of the cell culture chamber, the substrate comprising a plurality of microcavities and a layer of porous material, each microcavity of the plurality of microcavities comprising a concave surface defining a well and an opening defining a path from the first region into the well, wherein a first side of the layer of porous material defines at least a portion of the concave surface of each microcavity of the plurality of microcavities, and wherein a second side of the layer of porous material faces the second region and further wherein the layer of porous material is permeable to gas and impermeable to liquid to allow gas exchange with the second region; and
 a first aperture extending through the wall in fluid communication with the first region.

17. The cell culture vessel of claim 16, wherein the first side of the layer of porous material defines the entirety of the concave surface of each microcavity of the plurality of microcavities.

18. The cell culture vessel of claim 16, wherein each microcavity of the plurality of microcavities comprises a sidewall surface extending from the opening to the concave surface, and wherein the first side of the layer of porous material defines at least a portion of the sidewall surface of each microcavity of the plurality of microcavities.

19. The cell culture vessel of claim 18, the first side of the layer of porous material defines the entirety of the sidewall surface of each microcavity of the plurality of microcavities.

20. The cell culture vessel of claim 16, wherein the layer of porous material defines the entirety of the substrate.

21. The cell culture vessel of claim 16, further comprising a port extending through the wall in fluid communication with the second region, the port comprising a gas-permeable filter.

22. The cell culture vessel of claim 21, further comprising a conduit fluidly connecting the first region to the second region.

23. The cell culture vessel of claim 22, wherein an end of the conduit leading from the first region to the second region is positioned in the first region and spaced from the opening of each microcavity of the plurality of microcavities.

24. A method of culturing cells in the cell culture vessel of claim 22, comprising passing gas through the conduit connecting the first region to the second region, and culturing cells in at least one microcavity of the plurality of microcavities.

25. A method of culturing cells in the cell culture vessel of claim 21, comprising passing gas into the gas-permeable filter of the port, and culturing cells in at least one microcavity of the plurality of microcavities.

26. The cell culture vessel of claim 16, further comprising a conduit connecting the first aperture to the second region.

27. A method of culturing cells in the cell culture vessel of claim 26, comprising passing liquid through the conduit connecting the first aperture to the second region, and culturing cells in at least one microcavity of the plurality of microcavities.

28. The cell culture vessel of claim 16, further comprising a second aperture extending through the wall in fluid communication with the second region.

29. The cell culture vessel of claim 28, comprising a conduit connecting the second aperture to the second region.

30. A method of culturing cells in the cell culture vessel of claim 29, comprising:
   passing liquid through the first aperture; and
   culturing cells in at least one microcavity of the plurality of microcavities.

31. A method of culturing cells in the cell culture vessel of claim 29, comprising:
   passing liquid through the conduit connecting the second aperture to the second region; and
   culturing cells in at least one microcavity of the plurality of microcavities.

32. A method of culturing cells in the cell culture vessel of claim 28, comprising:
   passing liquid through the second aperture; and
   culturing cells in at least one microcavity of the plurality of microcavities.

33. A method of culturing cells in the cell culture vessel of claim 16, comprising:
   passing gas into the at least a portion of the concave surface defined by the first side of the layer of porous material of at least one microcavity of the plurality of microcavities; and
   culturing cells in the at least one microcavity.

34. A method of culturing cells in the cell culture vessel of claim 16, comprising:
   passing liquid through the first aperture from outside the vessel into the first region;
   depositing at least a portion of the liquid in at least one microcavity of the plurality of microcavities; and
   culturing cells in the at least one microcavity of the plurality of microcavities after depositing the at least a portion of the liquid in the at least one microcavity.

* * * * *